(12) United States Patent
Robertson

(10) Patent No.: US 6,592,737 B1
(45) Date of Patent: Jul. 15, 2003

(54) METHOD AND APPARATUS FOR DETERMINATION OF ADDITIVES IN METAL PLATING BATHS

(75) Inventor: Peter M. Robertson, Winkel (CH)

(73) Assignee: Advanced Technology Materials, Inc., Danbury, CT (US)

( * ) Notice: Subject to any disclaimer, the term of this patent is extended or adjusted under 35 U.S.C. 154(b) by 274 days.

(21) Appl. No.: 09/690,770

(22) Filed: Oct. 17, 2000

Related U.S. Application Data

(63) Continuation-in-part of application No. 09/421,658, filed on Oct. 20, 1999, now Pat. No. 6,280,602.

(51) Int. Cl.[7] .............................................. G01N 27/42
(52) U.S. Cl. .......................... 205/81; 205/83; 205/789; 204/434
(58) Field of Search ................................ 204/400, 409, 204/412, 416, 434; 205/789, 789.5, 81, 83; 702/22, 23

(56) References Cited

U.S. PATENT DOCUMENTS

| | | | |
|---|---|---|---|
| 4,479,852 A | 10/1984 | Bindra et al. ................. 205/81 |
| 5,192,403 A | 3/1993 | Chang et al. ............. 205/794.5 |
| 5,324,400 A * | 6/1994 | Eliash et al. ................. 205/794 |
| 5,635,043 A | 6/1997 | Tur'Yan et al. ............. 204/412 |
| 6,280,602 B1 * | 8/2001 | Robertson .................... 205/775 |

OTHER PUBLICATIONS

Freiting et al., Analysis of additives in Acid Copper Baths by Cyclic Voltammetry. Annu. Tech. Conf. Proc.—Am. Electroplat. Soc. (1983), 70th pp. 1–9.

* cited by examiner

*Primary Examiner*—Nam Nguyen
*Assistant Examiner*—Alex Noguerola
(74) *Attorney, Agent, or Firm*—Steven J. Hultquist; Margaret Chappuis

(57) ABSTRACT

An apparatus and method for the indirect determination of concentrations of additives in metal plating electrolyte solutions, particularly organic additives in Cu-metalization baths for semiconductor manufacturing. Plating potentials between the reference and test electrodes are measured and plotted for each of the solution mixtures, and data are extrapolated to determine the concentration of the additive in the sample. A multi-cycle method determines the concentration of both accelerator and suppressor organic additives in Cu plating solution in a single test suite.

37 Claims, 14 Drawing Sheets

METHOD AND APPARATUS FOR DETERMINATION OF ADDITIVES IN METAL PLATING BATHS

This is a Continuation of Ser. No. 09/421,658, filed Oct. 20, 1999, now U.S. Pat. No. 6,280,602.

BACKGROUND OF THE INVENTION

1. Field of the Invention

The present invention generally relates to the determination of additives in metal plating baths, and more specifically to a method and apparatus for determination of organic suppressor and accelerator additives in semiconductor copper electrolysis plating baths.

2. Background of the Invention

Traditionally, aluminum (Al) has been used as the material of choice for metalization in forming interconnect layers in the manufacture of semiconductor microelectronic integrated circuits. Al is commonly deposited on semiconductor structures by chemical vapor deposition (CVD), which allows for precise control and highly uniform deposition of the product metal-containing film.

Despite the prior ubiquity of Al as a metalization medium, performance demands associated with increasing signal speeds and decreasing feature geometries of microelectronics have exceeded the capabilities of Al metal. Copper (Cu) therefore is increasingly being utilized as a semiconductor interconnect metal. The properties of Cu are not amenable to conventional CVD metalization approaches, due in part to the lack of suitable copper source reagents, and in consequence Cu is typically deposited on the microelectronic device structure via electroplating.

Electroplating of copper, however, has various associated problems.

Generally, Cu is plated onto a substrate by electrolysis in an etch solution, which may for example comprise copper sulfate, sulfuric acid, and hydrochloric acid. The plating process with an unaugmented etch solution of such type normally proceeds too rapidly. The result of such plating rapidity is that previously formed vias, i.e., passages to lower-level structures, e.g., electrodes or other conductors or semiconductor regions in the microelectronic device structure, are bridged over, and not are filled with Cu. Accordingly, the desired electrical path to the underlying structure is not formed, and the semiconductor device structure must be reworked or discarded.

In order to combat such plating rapidity, the Cu plating process must be retarded. Additionally, the copper plating process requires acceleration in some aspects, to achieve desired coverage and leveling properties of the deposited metal. To achieve these simultaneously opposing goals, organic additives are introduced into the copper electroplating bath to both slow down the plating process (suppressor additives) and to speed it up (accelerator additives). The speed of deposition of Cu on the substrate, and the quality and resulting electrical and mechanical properties of the metalization, are critically dependent on the concentration of these organic additives in the copper electroplating bath. However, the concentration of these additives is not constant, due to either "drag-out" by the wafers or by electrochemical reaction and loss during the electroplating. Accurate, real-time measurement of these electroplating bath additive concentrations, necessary for quality control, has been problematic.

The respective suppressor and accelerator organic compounds in the copper electroplating bath are usually present at very low, e.g., part-per-million by volume (ppmv) concentrations. This circumstance makes normal analytical procedures difficult to effectively apply, due to the masking effect of the high concentration of inorganic bath components (copper, acid, etc.). The most effective way of determining these organic compounds is by measuring their effect on the amount of Cu deposited.

Methods of measuring the effect of the concentration of the electroplating suppressors and accelerators are known in the art. U.S. Pat. No. 5,192,403, issued to Chang et al. on Mar. 9, 1993, describes one such method, comprising the steps of:

a) preparing a basis solution which contains all of the components of the plating solution to be measured (the "sample"), except the component of interest;

b) preparing a calibration solution which contains the component of interest in a known concentration near that which would be expected in the sample;

c) adding measured amounts of the calibration solution to a first defined volume of the basis solution, and plotting the copper plating (cathodic) charge in cyclic voltammetry in the mixed solution against the added volume of the calibration solution;

d) adding measured amounts of the sample solution to a second volume of the basis solution, and plotting the copper plating (cathodic) charge in cyclic voltammetry in the mixed solution against the added volume of the sample; and e) comparing the slopes of the calibration standard curve and the sample mixture curve to determine the concentration of the component of interest in the sample solution.

Variations of this technique are employed in the art to measure the concentrations of organic suppressor and accelerator additives in Cu electroplating baths for semiconductor manufacturing. These techniques variously measure the plating charge or stripping (de-plating) charge, e.g., for electro-plate deposition of Cu directly onto a test electrode via current supplied to a counting electrode in a plating step, and removal of previously plated copper in a stripping step. The charge is generally obtained by measuring the plating or stripping current while holding the voltage constant, and integrating to obtain the charge (the potentiostatic method). Typically, an electrode is cyclically plated and de-plated (stripped of the previously deposited Cu) multiple times for each quantity measured. Each plating/measurement cycle comprises the following steps:

Clean—the test electrode surface is thoroughly cleaned electrochemically or chemically using acid bath, followed by flushing with water or acid bath, Equilibrate (optional)—the test electrode and a reference electrode are exposed to the plating electrolyte and allowed to reach an equilibrium state.

Plate—Cu is electroplated onto the test electrode either at constant potential or during a potential sweep and the current between the test and counter electrodes is monitored and recorded, and Strip—the Cu deposition is removed (e.g., by reversal of the plating current flow and/or exposure to an acid bath) by suitably changing the potential between the test and counter electrodes stepwise or in a sweep in the reverse direction, with the current between the test and the counter electrode being monitored and recorded (and integrated to determine the "stripping charge").

Prior art methods typically utilize the potentiostatic method described above, wherein the electrolysis potential is held constant, and the plating current is measured and integrated to obtain the plating charge. Alternatively, the galvanistatic method maintains a constant or controlled current during plating, and the plating potential or overpotential between the test and reference electrodes is measured. The overpotential is defined as the difference between the decisive potential, measured during plating at a constant current, and the equilibrium potential, measured following the plating step with the zero current flow in the electroplating circuit.

These four steps must be repeated for each plating/measurement cycle; each sample measurement is typically repeated several times to eliminate random errors introduced by variations in process conditions, e.g., composition, temperature, etc. Even when errors are thus averaged out, however, the conditions under which metal deposition is performed are often sub-optimal, resulting in unreproducible deposits and plating data.

An entire concentration determination sequence can require a considerable period of time to complete. To be useful as a quality control tool in copper metalization in semiconductor manufacturing, the concentration determination must be completed in a very short time frame so that significant depletion of the organic additives in the plating bath does not occur. Any significant depletion of organic additives during the determination will render the analytical method useless.

It would therefore be a significant advance in the art, and is accordingly an object of the present invention, to significantly reduce the time required for the concentration determination sequence to be completed, relative to the present state of the art.

To allow for fine control of the plating process, it is also desirable that concentration of organic additives be determined to a high degree of accuracy. It therefore is a further objective of the present invention to determine the organic additive concentrations to a high degree of precision, preferably to less than 10 percent of indicated value, and more preferably to less than about five percent of indicated value.

Consistent, even, and highly reproducible plating operations onto the test electrode significantly enhance the efficacy and accuracy of metal electroplate bath additive concentration measurements by providing uniform, repeatable data sets from which to construct calibration curves. It is thus a further object of the present invention to provide a test electrode plating method that significantly enhances the uniformity and repeatability of plating current, charge, potential, or overpotential data.

It is another object of the invention to provide an improved system for determination of organic additive concentration in a copper electroplating bath, that is simple in operation, economic in capital cost and operating expense, and efficient in characterization of the electroplating medium.

Other objects and advantages will be more fully apparent from the ensuing disclosure and appended claims.

SUMMARY OF THE INVENTION

The present invention relates in one aspect to an apparatus for the determination of concentrations of organic additives in a Cu electroplating bath, comprising:

a reference electrode, housed in an electrically isolated reference chamber and immersed in a base metal plating solution;

a test electrode having a plating surface upon which metal is depositable by electroplating, deposited in a measurement chamber containing an electroplating current source electrode, wherein metal plating solutions containing known and unknown concentrations of additives are introduced to, and intermixed with, the base metal plating solution to form a mixed metal plating solution;

a capillary tube joining the reference chamber and the mixing chamber in unidirectional fluid flow relationship, whereby base metal plating solution is transferred to the measurement chamber from the reference chamber, and wherein the measurement chamber end of the capillary tube is deposed in close spatial relationship to the plating surface of the test electrode;

selectively controllable electroplate driving electronics electrically and operatively coupled between the test electrode and the electroplating current source electrode, for selectively effectuating deposition of metals onto the test electrode from the mixed metal plating solution in the measurement chamber, wherein said electroplating driving electronics have two selectable modes, the first mode for providing an initial high plating current density for a short duration, and the second mode for providing subsequent constant or known current density for a duration sufficient to measure electrical potential; and electrical potential measuring circuitry electrically and operatively coupled between the test electrode and the reference electrode, whereby electrical potential between the test electrode and the reference electrode is measured and recorded.

The present invention relates in another aspect to a method for measuring the characteristic decisive potential of a mixed metal plating solution by performing a plating/measuring cycle, comprising:

cleaning the test electrode and measuring chamber, e.g., by a method selected from the group consisting of acid bath exposure, electrolytic cleaning with or without gas (oxygen) generation, water flush, forced fluid purge, and combinations thereof, flowing a first known volume of base metal plating solution which contains all components of the mixed metal plating solution to be measured except a component of interest from the reference chamber through the capillary tube into the measurement chamber;

optionally adding to the measurement chamber a second known volume of metal plating solution containing a certain concentration, either predetermined or unknown, of the component of interest and mixing the solutions;

allowing the test electrode to come to an equilibrium state in the mixed metal plating solution, such that there exists no electrical perturbation between the reference electrode and the test electrode and that no electric current flows to or from the test electrode;

stimulating the growth of metal nuclei on the test electrode by applying an initial high plating current density for a short duration to begin the electroplating cycle, and subsequently maintaining a stable deposition of metal onto the test electrode from the mixed metal plating solution in the measurement chamber by electroplating at a constant or known current density which is relatively lower than the initial current density;

measuring and recording the decisive electrical potential characteristic of the mixed metal plating solution between the reference electrode and the test electrode at a set time after initiation of the plating step, whereby sufficient stability of metal deposition has been reached;

measuring and recording the equilibrium electrical potential between the reference electrode and the test electrode following completion of the plating process, whereby electric current flow in the electroplating circuit is zero;

calculating the over-potential by subtracting the equilibrium potential from the decisive potential; and stripping the deposited metal from the test electrode, e.g., by a method selected from the group consisting of chemical stripping, application of reverse bias electroplating current, and combinations thereof.

The present invention relates in another aspect to a method for conditioning the base plating solution for the determination of organic additives in metal plating solutions, comprising:

adding to the first known volume of base metal plating solution in the measuring vessel a known volume of additive and performing plating and stripping operations, whereby the non-linearity of the response of the decisive potential to the additive is "masked," and all decisive potential measurements are carried out in the linear region of the response, this optional conditioning of the base metal plating solution being performed prior to the introduction of the sample to be determined.

The present invention relates in another aspect to a method for calculating the concentration of organic additives in metal plating solutions from the measured characteristic property of a plurality of metal plating solutions containing various known concentrations of the organic additives to be measured, comprising:

plotting values calculated as the inverse of the ratio of the measured potential of each metal plating bath solution containing additives to the measured potential of the metal plating bath solution containing the sample, minus one;

linearly extrapolating back through these points to determine the point corresponding to the value of the inverse of the expression:

[(the measured potential of metal plating for that solution, with no additives)/(the measured potential of metal plating for that solution, containing the sample)]-1; and calculating the negative inverse of the value.

The present invention is based in part on applicant's discovery of a technique to dramatically reduce equilibration time of the reference electrode in an apparatus for the determination of concentration of additives by the Pulsed Cyclic Galvanostatic Analysis (PCGA) technique. In conventional practice, a reference electrode is placed in the same electrolyte solution as is the test electrode upon which Cu is deposited. Following each plating/measurement cycle, the test electrode must be stripped of the deposited Cu, and cleaned to remove all traces of the test solution (which contains some level of additive). The test electrode and the reference electrode are then re-immersed in the base copper plating electrolyte solution, and must return to an equilibrium state prior to initiation of the next plating/measurement operation.

In one embodiment of the present invention, the reference electrode resides in a reference chamber that is physically and electrically isolated from the measurement chamber that houses the test electrode (upon which Cu is deposited). The reference electrode is continuously immersed in the base copper plating electrolyte solution. By never exposing it to the variously doped bath solutions in the measurement chamber, the reference electrode need not be cleaned following each plating/measurement cycle. Thus, it remains continuously "equilibrated" to the base copper plating electrolyte solution, and the equilibration step is reduced to the time necessary for the test electrode to "equilibrate" to a fresh base copper plating electrolyte solution. This reduces the equilibration step by roughly an order of magnitude over the prior art, i.e., to seconds.

The reference chamber is connected in fluid flow relationship to the measurement chamber by a capillary tube, whose measurement chamber terminal end is in close physical proximity to the plating surface of the test electrode. By this arrangement, the apparatus of the present invention achieves several additional advantages, including:

Potential difference (iR drop) across the electrolyte is eliminated or dramatically reduced.

The measurement chamber is filled with base copper plating electrolyte solution for each cycle through the capillary tube, from the reference chamber. Both electrodes are hence initially immersed in the same electrolyte.

The flow of base copper plating electrolyte solution through the capillary tube and against the plating surface of the test electrode facilitates the removal of air on the test electrode, contributing to consistent cycle-to-cycle measurements.

The flow of base copper plating electrolyte solution through the capillary tube generates a fresh and reproducible liquid junction to the measuring vessel.

Another significant feature of the present invention is the pulse nucleation process of applying a brief, intense plating current density to stimulate the generation of plated metal growth centers, or nuclei, at the beginning of the plating cycle, which can significantly increase the linearity and reproducibility of the metal plating process.

In either the potentiostatic or galvanistatic method, measurements of the effect of additives on the electroplating of a test electrode are taken, and regression analysis of the resulting data is performed to determine the concentration of additives in a sample. A significant problem with these methods is that the metal deposition is performed under a variety of conditions, most of which are sub-optimal and produce unreproducible metal deposits and thus unreproducible plating data. One reason for this is a very large sensitivity in the measured quantity (i.e., plating decisive potential or over-potential) to very small amounts of some additives when such additives are first introduced into the metal plating solution, and the lower sensitivity of that measured quantity once the additive is present in the metal plate bath. The resulting non-linear curve makes it difficult to determine the additive concentration by standard addition or other calibration techniques, such as regression of a calibration line. Additionally, excessive scatter of data points on the standard addition curves results in a large uncertainty factor due to poor repeatability.

In a metal plating process the initial deposition of growth centers dictates the way the metal deposition process proceeds. If this initial process can be carried out reproducibly, the entire plating process is similarly affected and reproducible data is obtained. It has been discovered that the reproducible generation of growth centers, or nuclei, can be effectuated by applying a very high plating current density for a very short duration (in the millisecond range) at the beginning of the plating cycle. Following application of this initial nucleation pulse, the metal is then plated at the recommended constant, known current density and the relevant parameters are measured and recorded while the plating process reaches certain stability.

This two-phase plating process results in unexpectedly improved performance and accuracy of the measurement process, and represents a significant advance in the state of the art. The first phase, the nucleation pulse, generates sites for the growth of the copper film in a consistent and reproducible manner; the second phase, plating at the recommended current density, proceeds with a uniform, consistent, and reproducible deposition of copper, allowing for more accurate and reproducible measurements. A particular advantage of this technique is that the non-linear behavior of the system is eliminated, and the whole plating potential range, i.e., from suppression-free to fully suppressed in the case of suppressor additives, is available for the measurement. Another significant advantage of this pulsed nucleation technique is that the excessive scatter on the standard addition curves is limited to a minimum amount and thus highly reproducible and accurate data is generated for reliable regression of the sample concentration of the metal plating additives.

In this two-phase electroplating process, the initial current density of the nucleation pulse is high, preferably in the range 10 mA/cm$^2$ to 10 A/cm$^2$, and most preferably about 400 mA/cm$^2$; the current density of the subsequent second phase of the plating process is lower and in the range recommended by the bath manufacturer, preferably in the range 1 mA/cm$^2$ to 50 mA/cm$^2$, and most preferably about 10 mA/cm$^2$. The temporal duration of the nucleation pulse is short, preferably in the range 1 msec to 1000 msec, and most preferably in the range about 40 msec to 200 msec; the duration of the second phase is longer, preferably in the range 1 sec to 100 sec, and most preferably about 10 sec.

The plating current density and the plating duration of each phase of the plating process of the present invention, and particularly the second phase, may be varied by those of ordinary skill in the art without undue experimentation, within the broad practice of the present invention, to achieve consistent and reproducible metal plating parameter measurements and data.

Moreover, because the nucleation pulse technique eliminates the non-linear behavior of the system, accurate measurement can be effectively obtained for the whole plating response range, i.e., from zero additive concentration to high additive concentration. It is therefore another aspect of the present invention to employ interpolative analytical method rather than extrapolative analytical method in data treatment to achieve more accurate determination of the organic additive concentration in the sample metal plating solution.

An interpolative analysis for determining the concentration of an organic additive in a sample of metal plating solution can be done by:

preparing a basis metal plating solution which contains all components of the sample plating solution to be measured, except the component of interest, or optionally to which has been added a known volume of the component of interest;

preparing a plurality of calibration solutions in various concentrations of the organic additive, ranging from below to above that which would be expected in the sample solution;

firstly performing a plating/measuring cycle in the base solution, and measuring the decisive potential characteristic of the basis solution;

then adding a measured amount of the first calibration solution to a known volume of the basis solution, performing a plating/measuring cycle including an initial nucleation pulse in the mixed solution, and measuring the decisive potential characteristic of the mixed solution;

repeating the above step for each calibration solution, measuring the decisive potential of each;

then adding a measured amount of the sample solution to the same volume of fresh basis solution, performing a plating/measuring cyclic including an initial nucleation pulse in the mixed solution, and measuring the decisive potential characteristic of the mixed solution;

using data obtained from the measurements of the basis solution and the calibration solutions to build up a fill decisive potential curve characteristic of the organic additive; and using the decisive potential measured for the sample solution to interpolate the concentration of the organic additive in the sample solution from the already fitted decisive potential curve.

A further aspect of the present invention relates to a method of determining concentrations of both an accelerator additive and a suppressor additive in a sample of copper-metal plating solution, comprising the steps of:

preparing a basis copper plating electrolyte solution containing all of the components of the sample copper plating solution to be measured, except the accelerator and the suppressor additives, or optionally conditioning such basis solution with a known and small volume of the suppressor additive;

preparing plurality of standard additions containing either suppressor additive or accelerator additive, each of which containing suppressor or accelerator in a unique, known concentration;

performing measurement for the suppressor additive concentration determination in a known and fixed volume of basis solution, comprising background measurement of the basis solution and measurement of the sample and standard addition solutions containing the suppressor additive;

adding an excess amount of suppressor additive to the same volume of fresh basis copper plating solution, using such as the basis solution for the measurement for the accelerator additive concentration determination;

performing measurement for the accelerator additive concentration determination in the same volume of fresh basis solution containing the excess amount of suppressor additive, comprising background measurement of the basis solution and measurement of the sample and standard addition solutions containing the accelerator additive; and separately determining the sample concentrations of suppressor additive and accelerator additive by performing extrapolation or interpolation analysis upon data obtained during measurement for the suppressor concentration determination and measurement for the accelerator concentration determination.

Additional aspects, features and embodiments of the invention will be more fully apparent from the ensuing disclosure and appended claims.

DETAILED DESCRIPTION OF THE INVENTION, AND PREFERRED EMBODIMENTS THEREOF

The apparatus of the present invention utilizes a reference electrode housed in a reference chamber and continuously immersed in a base copper plating electrolyte solution; a test electrode upon which Cu is deposited and removed in each plating/measurement cycle, deposed within a measurement chamber wherein various solutions containing additives are introduced to the base copper plating electrolyte solution; a capillary tube joining the reference chamber and the measurement chamber in unidirectional fluid flow relationship, for introducing fresh base copper plating electrolyte solution into the measurement chamber for each plating/measurement cycle, wherein the measurement chamber end of the capillary tube is deposed in close physical proximity to the plating surface of the test electrode; and driving electronics operationally coupled to the test and plating current source electrodes and measurement electronics operationally coupled to the reference electrode and the test electrode.

Figure 1:
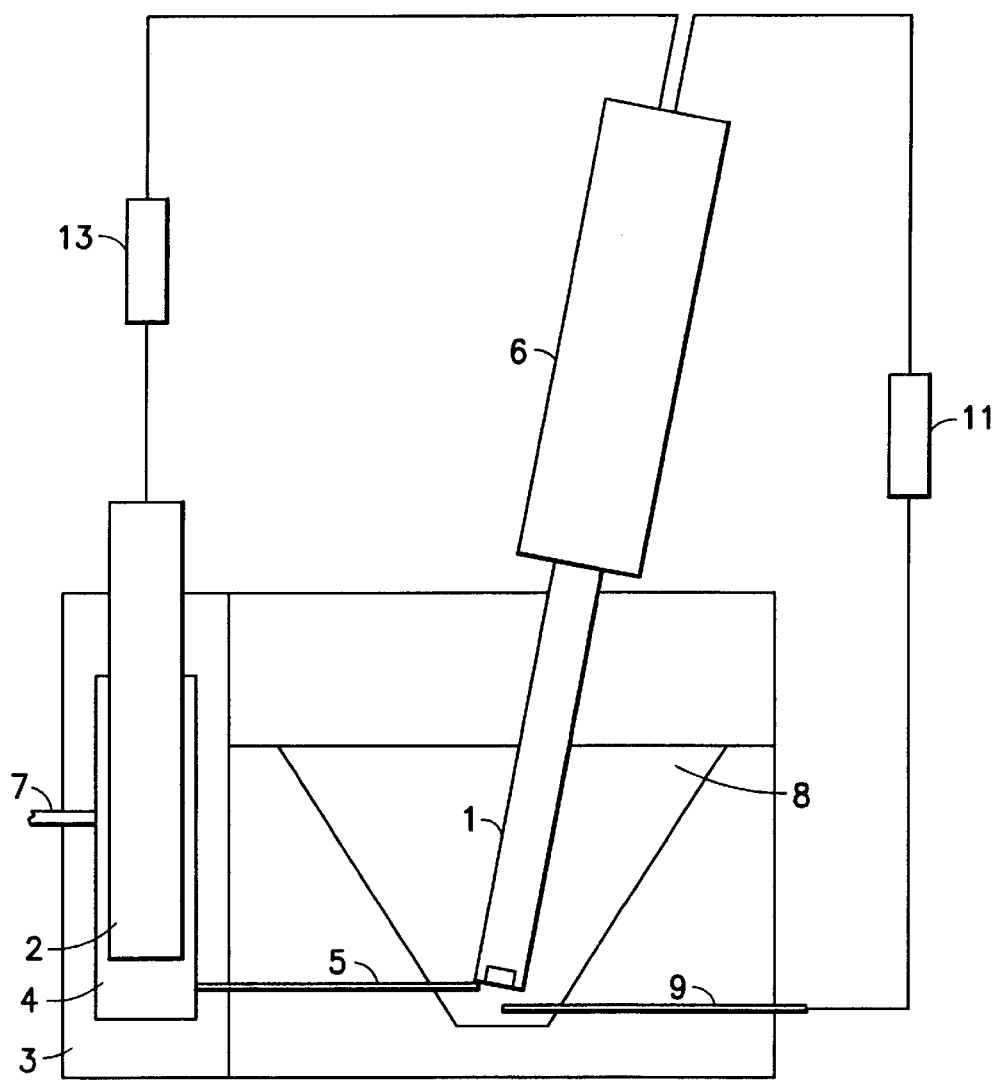
FIG. 1 is a schematic representation of a system of the present invention according to one embodiment thereof.

Referring to FIG. 1, reference electrode 2 is deposed in reference chamber 3, and continuously immersed in base copper plating electrolyte solution 4. Base solution 4 is injected into reference chamber 3 through fluid flow inlet 7, and flows into measurement chamber 8 via capillary tube 5. Additional solutions containing additives (sample solution and calibration solution(s)) are introduced into the measurement chamber (through means not depicted in FIG. 1) and thereby mixed with the base copper plating electrolyte solution introduced therein through capillary tube 5. Fluid pressure differential, and/or fluid flow valves prevent the propagation of mixed electrolyte solution from measurement chamber 8 to reference chamber 3. Thus, reference electrode 2 is continuously, exclusively immersed in base copper plating electrolyte solution 4.

The measurement chamber end of capillary tube 5 is deposed in close proximity to the plating surface of test electrode 1, preferably within a few millimeters. This close spatial relationship prevents air bubble formation on the plating surface of test electrode 1, and reduces or eliminates the effect of electrical potential difference (iR drop) in the electrolyte. Plating current source electrode 9 is electrically and operatively coupled to test electrode 1 through a suitable, reversible, controllable current source 11. The current source 11 provides driving forces for selectively depositing metals onto the test electrode 1 from the mixed metal plating solution in the measurement chamber 8, and such current source suitably has two selectable modes, one for providing an initial high plating current density for a short duration, and the other for providing subsequent recommended constant current density for a longer duration sufficient to measure electrical potential.

Test electrode 1 is preferably comprised of a platinum or glassy carbon (vitreous carbon) substrate, although it is not restricted to these materials. Test electrode 1 is preferably mechanically and electrically coupled to rotational driver 6, or driver 6 and electrode 1 may be combined in a unitary rotating disc electrode, as is known in the art. Use of a rotating disk electrode increases the accuracy and consistency of measurements across cycles by stirring the electrolyte solution contained in the measurement chamber.

Alternatively, test electrode 1 may be an ultra-micro electrode with diameter less than 50 microns and preferably less than 10 microns where forced agitation of the electrolyte mixture within measurement chamber 8 is not necessarily required.

As a still further alternative, a small-scale mixer, ultrasonic vibrator, mechanical vibrator, propeller, pressure differential fluid pump, static mixer, gas sparger, magnetic stirrer, fluid ejector, or fluid eductor may be deployed in the measurement chamber 8, to effect hydrodynamic movement of the fluid with respect to the test electrode.

In all embodiments, test electrode 1 is preferably tilted at an angle from vertical, to prevent the collection and retention of air bubbles on its surface. Such angle is preferably between 3 and 45 degrees. Suitable means 13 for measuring electrical potential between the test electrode and the reference electrode are employed, and such means are readily implemented within the skill of the art.

Suitable means for purging electrolyte solution from measurement chamber 8 following completion of each plating/measurement cycle, while not shown in FIG. 1, are employed, such means being readily implemented within the skill of the art. Additionally, acid bath or rinsing water thereof may be injected into and drained from measurement chamber 8. Suitable means for introducing electrolyte solutions containing additives (sample or calibration solutions) into measurement chamber 8, as well as suitable means for purging measurement chamber 8 of electrolyte solutions, and a forced fluid purging means may optionally be provided. These ancillary functions are easily provided by means well known in the art, and are not shown in FIG. 1 or discussed at length in the present disclosure.

Figure 2:
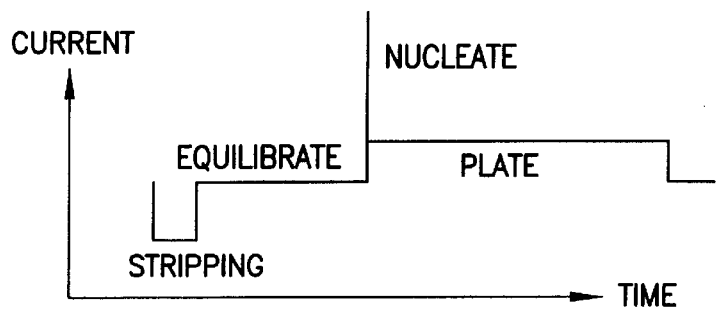
FIG. 2 is a graph depicting the four steps of a PCGA cycle.

The organic additive concentration determination method of the present invention is an adapted methodology of Pulsed Cyclic Galvanostatic Analysis (PCGA). PCGA is utilized in connection with the apparatus of the present invention to perform multiple plating/measurement cycles in mixed electrolyte solutions containing various known and unknown concentrations of additives. In each plating/measurement cycle, the test electrode and measuring chamber are first thoroughly cleaned, e.g., electrolytically in an acid bath followed by a water and/or forced air flush. Base electrolyte solution is then introduced into the measuring chamber from the reference chamber, mixed with other electrolytes (containing additives), and the test electrode allowed to equilibrate. Cu is then deposited onto a plating surface on the test electrode by a two-phase electroplating process in the mixed electrolyte solution, initially at a very high plating current density for a short duration, and then at a known or constant current density. The deposited Cu is then stripped from the test electrode by reverse biasing the electroplating circuit and/or by chemical stripping. Measurements of electrical potential between the test and reference electrodes are recorded throughout the cycle. The four basic steps of each cycle—Clean, Equilibrate, Plate, and Strip—and the associated measured potentials are depicted in the graph of FIG. 2.

A single plating/measurement cycle of the PCGA technique performed with the apparatus of the present invention comprises the following steps:

1) The test electrode and measurement chamber are cleaned by an acid wash followed by a water flush and/or a forced air purge.
2) Fresh base copper plating electrolyte solution is introduced to the measurement chamber from the reference chamber through the capillary tube.
3) Solutions of copper plating electrolyte variously "doped" with organic additives (according to the methodology of the present invention) are introduced to, and intermixed with, the base copper plating electrolyte solution in the measurement chamber.
4) Following equilibration of the test electrode, Cu is deposited via electroplating onto the test electrode beginning with a nucleation pulse, applying a very high plating current density for a short duration (i.e., milliseconds). Electroplating onto the test electrode then proceeds at a known or constant current density for a set time sufficient to ensure stability, and the electrical potential between the test electrode and the reference electrode is measured and recorded (the "decisive potential"). A significant feature of the apparatus and method of the present invention is that the reference electrode, being continuously exclusively immersed in fresh base copper plating electrolyte solution, requires no equilibration, hence significantly reducing the overall cycle time. A further significant feature of the apparatus and method of the present invention is the application of a nucleation pulse, which generates metal plate growth centers (nuclei) on the test electrode that result in subsequently uniform and repeatable copper deposition.
5) Following the plating step, with zero current flow in the electroplating circuit, the electrical potential between the test electrode and reference electrode is again measured and recorded (the "equilibrium potential"). The over-potential is determined by subtracting equilibrium potential from the decisive potential.
6) The deposited Cu is stripped from the test electrode by reversed biasing the plating circuit, and/or the introduction of chemical stripping agents into the measurement chamber. The electrical potential between the test electrode and reference electrode is again measured and recorded (the "stripping potential").

Concentrations of organic additives in copper plating electrolyte baths can be calculated extrapolatively, according to the multiple-plating/measurement cycle technique of Pulsed Cyclic Galvanostatic Analysis (PCGA). In general, PCGA comprises the following steps, wherein each step calling for a plating/measuring cycle is actually performed multiple times (e.g., four times) and the results averaged, to eliminate random errors:

1) preparing a base copper plating electrolyte solution ("basis solution") which contains all of the components of the plating solution to be measured (the "sample"), except the component of interest;
2) preparing a plurality of calibration solutions each of which contains the component of interest in a known concentration ("standard addition") in excess of that which would be expected in the sample;
3) performing a plating/measuring cycle, including an initial nucleation pulse, in the basis solution and optionally adding a known volume of additive (suppressor) in order to eliminate non-linear response behavior, and measuring the electrical potential between the test electrode and reference electrode at a set time after beginning the plating phase (the "decisive potential"), and again following the plating step, with zero current flow in the electroplating circuit (the "equilibrium potential"), and calculating the over-potential by subtracting equilibrium potential from the decisive potential.
4) adding a measured amount of the sample solution to a known volume of the basis solution, performing a plating/measuring cycle including an initial nucleation pulse in the mixed solution, and measuring the decisive potential and the over-potential of the mixed solution.
5) adding a measured amount of the first calibration solution (containing the first standard addition) to the same volume of fresh basis solution, performing a plating/measuring cycle including an initial nucleation pulse in the mixed solution, and measuring the decisive potential and the over-potential of the mixed solution;
6) repeating step 5 for each calibration solution, containing each standard addition; and
7) plotting the reciprocals of the decisive potentials and/or the over-potentials measured on a reciprocal concentration scale, and performing a linear extrapolation back to the basis measurement to obtain the negative reciprocal of the sample concentration of the component of interest.

As an aid to a more complete understanding of the invention, a formulistic representation of the data transformation and plotting method of step 7 above is set out below:

| Notation: | m1 basis measurement |
| | m2 sample measurement |
| | m3 first standard addition measurement |
| | m4 second standard addition measurement |
| Transformation: | |
| response | concentration |
| $m3' = 1/(m3/m2 - 1)$ | 1/standard addition one |
| $m4' = 1/(m4/m2 - 1)$ | 1/standard addition two |
| $m1' = 1/(m1/m2 - 1)$ | $-1$/sample |

The data points at m3' and m4' are linearly extrapolated back to m1' and the negative reciprocal sample concentration is thereby obtained.

The said method of data treatment can, however, be replaced by a more conventional one such as a polynomial curve fitting of the response as a function of the volume of additive added with an extrapolation back to zero response, which give the negative additive concentration in the sample.

Some additives, which give high instrumental response at very low concentrations and level off to a limiting response at high concentration, are difficult to determine at high concentration in the absence of a theoretical or empirical description of the non-linearity of response. Because of the initially large response at very low concentration and much less sensitivity at high concentration, standard addition methods of calibration and simple polynomial fitting can fail to give the correct extrapolation. However, if an addition of the active substance is done before any background or sample determination is performed the response curve is shifted to the linear and less sensitive region, which allows an easier determination to be made with much lower extrapolation error.

This method is particularly applicable for the determination of surface active compounds used in metal plating processes—in particular the so-called "suppressors" or "carriers" used in electroplating of metals. These substances have a great effect on the electro-deposition at very low concentrations because of the great affinity to form a monolayer at he electrode interface.

Figure 3:
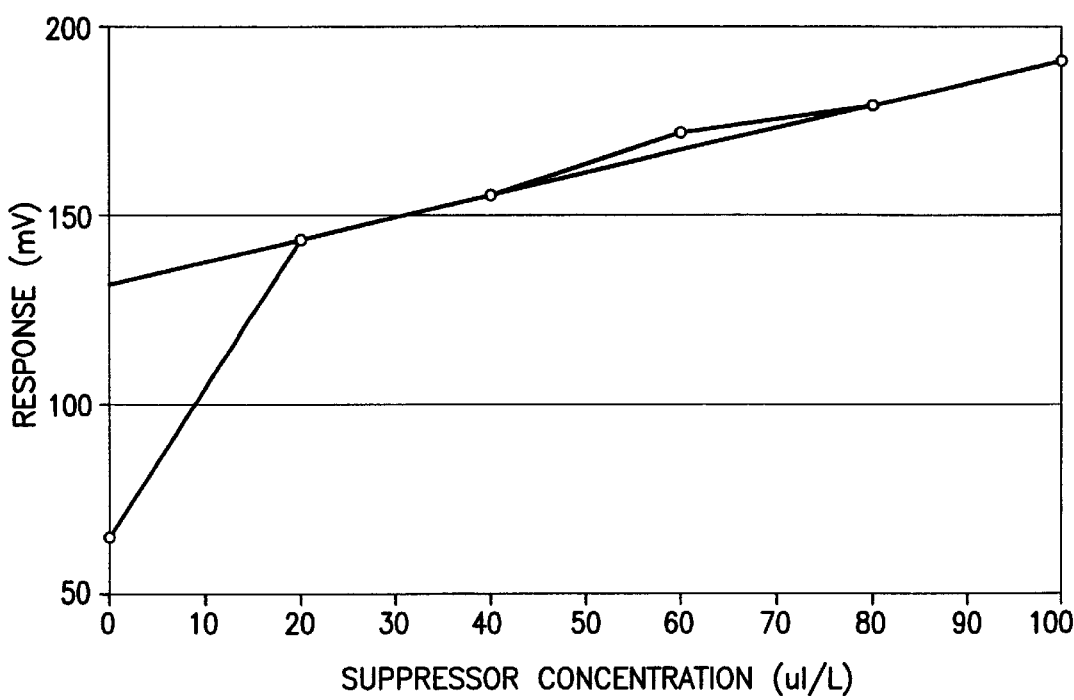
FIG. 3 is a graph depicting the non-linear and linear areas of the response curve for some types of additives.
Figure 4:
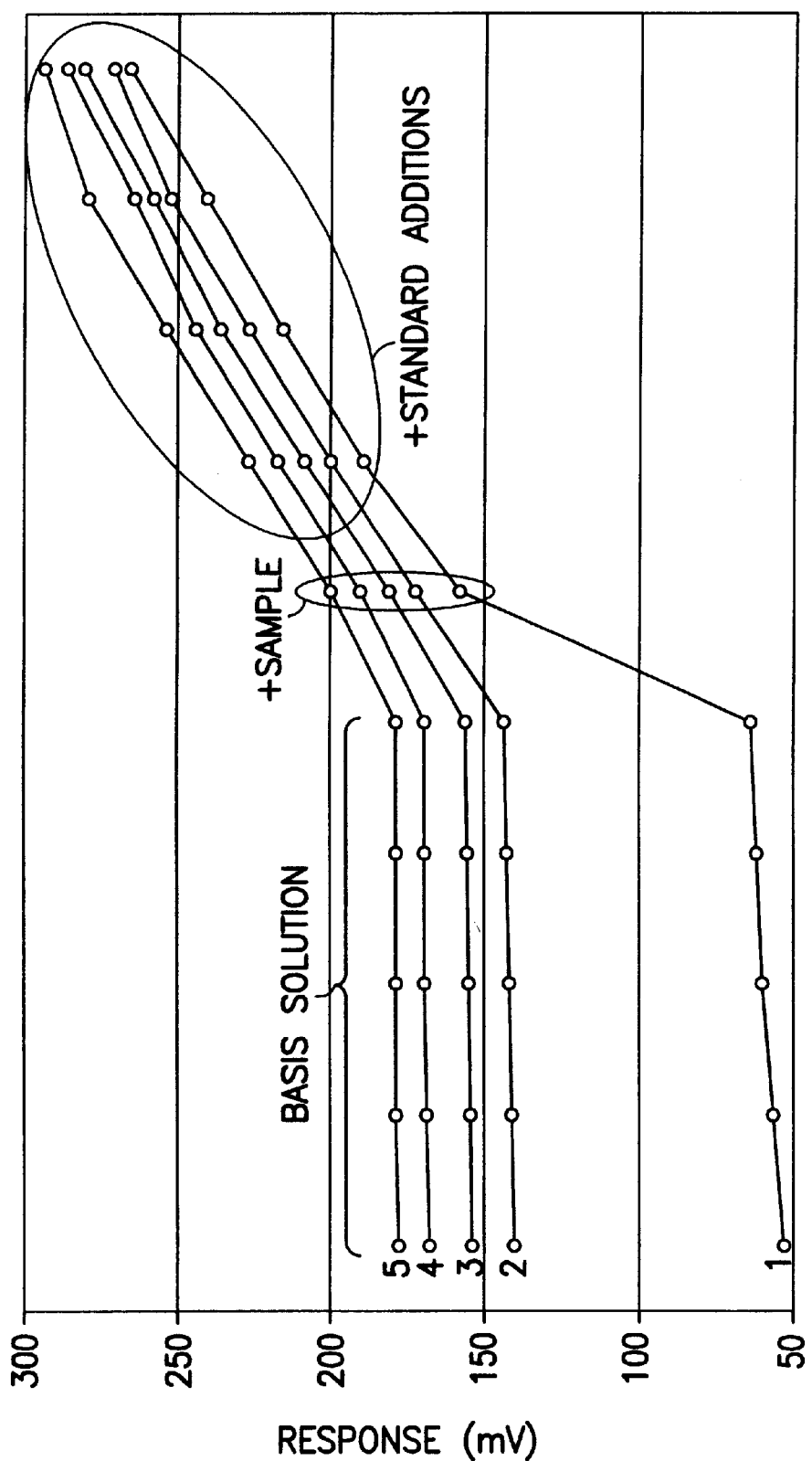
FIG. 4 is a graph depicting the non-linear and linear response curves of various concentrations of certain additive measurements.

An example of such a system and its response is depicted in graph of FIG. 3. At suppressor concentrations below 20 uL/L a very large change of response is observed, and above this concentration the response is almost linear (with "tailing-off" into a plateau region). Although the response in the "linear" region at concentrations above 20 uL/L shows a lower sensitivity to the suppressor concentration, this is desirable since typical plating bath compositions have the suppressor at extremely high concentration (25 mL/L). Hence, in the broad practice of the present invention to determine the concentrations of such additives, the initial "background" measurement may not be performed in a base metal plating electrolyte solution totally lacking the additive, but instead may be performed in a metal plating electrolyte solution containing a sufficient added concentration of the additive to generate a measured response in the linear region of the response curve. Successive measurements would then be performed in metal plating electrolyte solutions to which the sample or additional standard additions (calibration amounts) of additive were introduced in addition to the initial additive amount. The graph of FIG. 4 shows a comparison of some determinations without suppressor conditioned basis (background) solution (curve 1) and with suppressor conditioned basis solutions at concentrations of 20, 40, 60, and 80 uL/L (curves 2 through 5, respectively).

Figure 5:
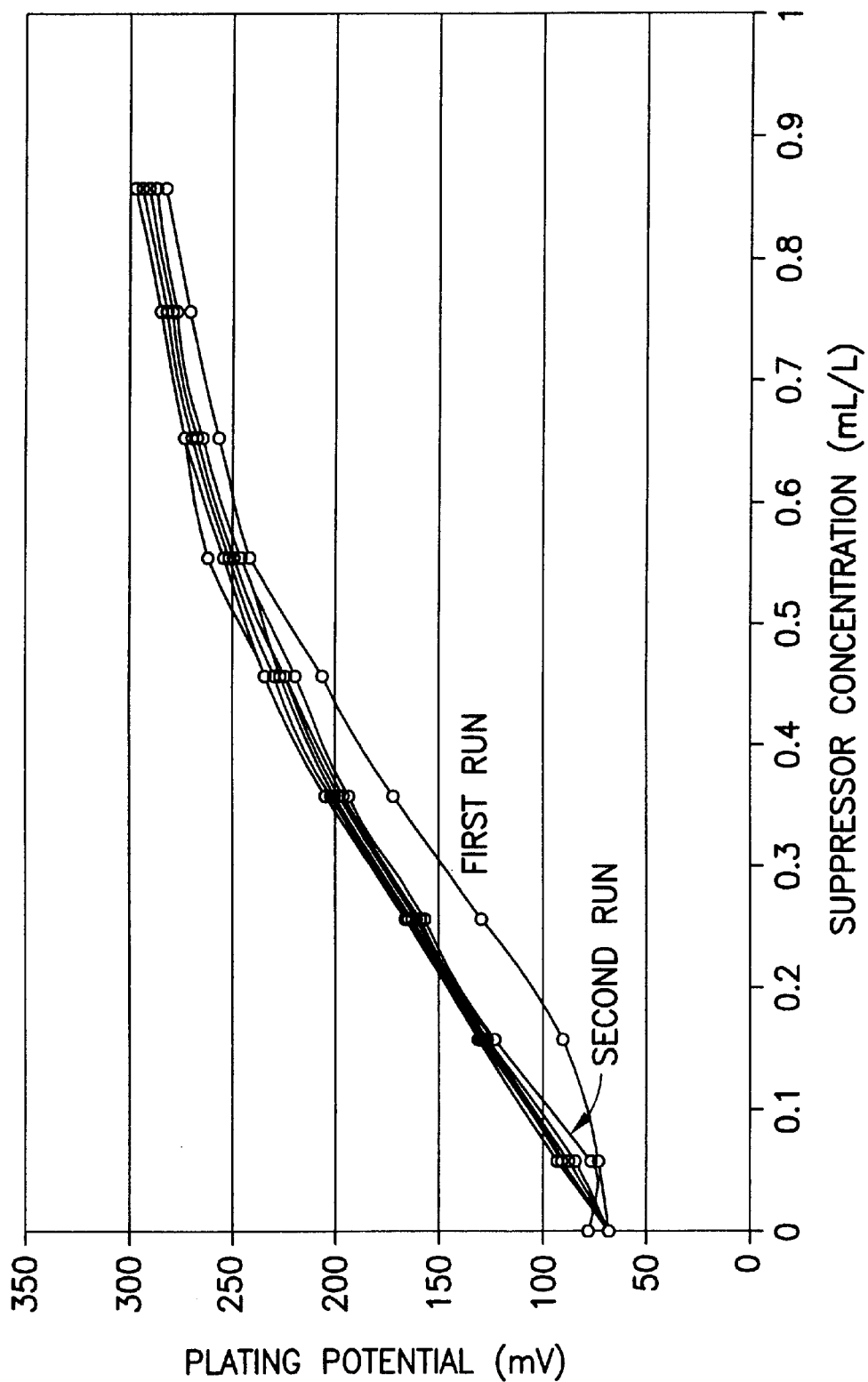
FIG. 5 is a graph depicting the enhanced linearity of response curves utilizing the nucleation pulse technique.

Alternatively, or additionally, the linearity of the suppressor additive response curve may be improved by use of the two-phase plating process, including an initial nucleation pulse to stimulate copper growth nuclei on the test electrode prior to copper deposition and the measurement of corresponding plating potential. FIG. 5 depicts the response curves of repeated suppressor additive measurements, the first run being performed without the nucleation pulse, and the second and subsequent runs being performed utilizing a nucleation pulse. As a FIG. 5 depicts, the measurements taken utilizing the nucleation pulse evidence not only a high repeatability, but also known as high linearity throughout the range from no suppressor to fully suppressed.

Figure 6A:
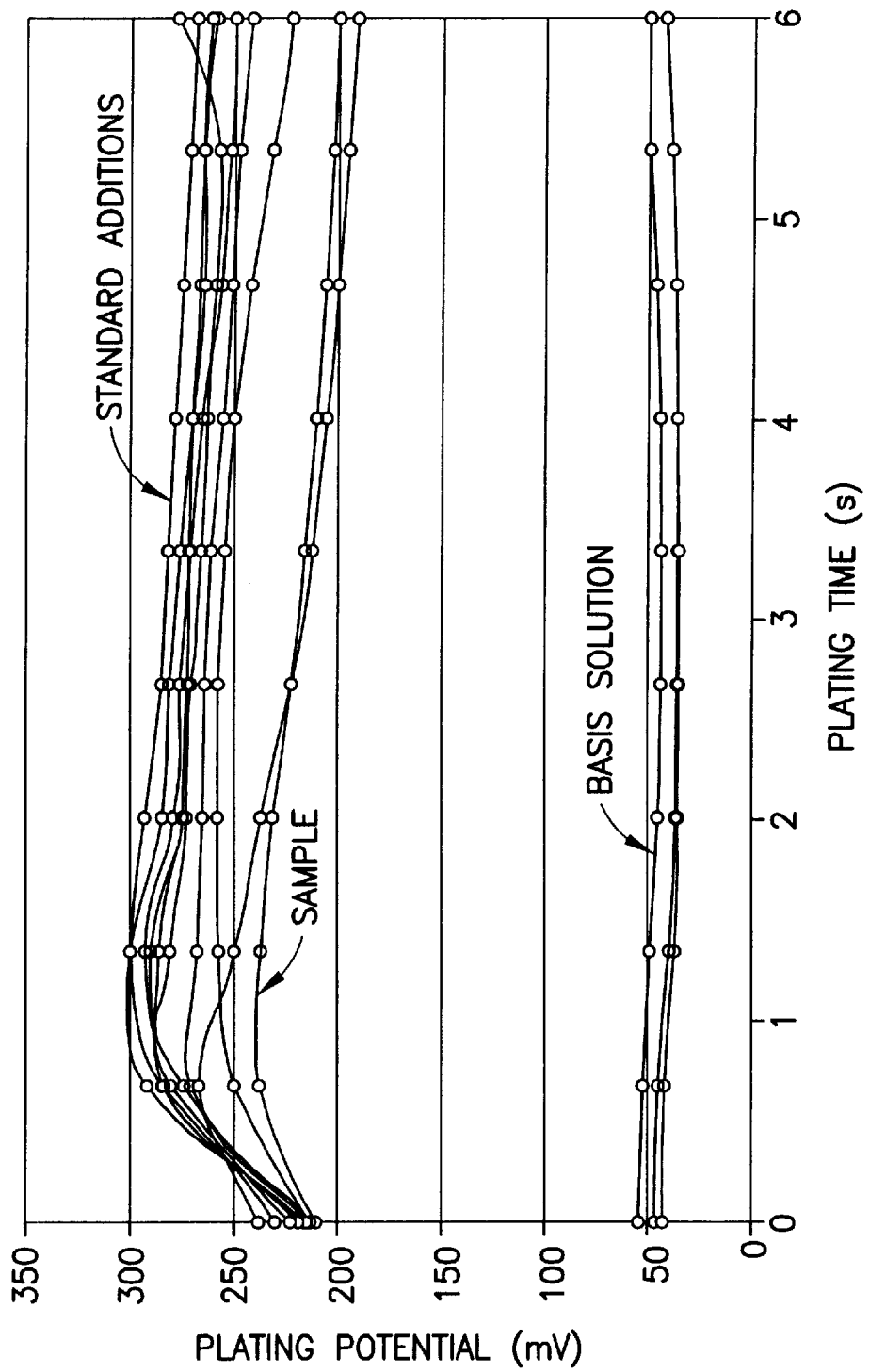
FIG. 6A is a graph depicting base, sample, and standard addition response curves to suppressor additive concentration determination with no nucleation pulse.

In addition to improving the linearity of the suppressor response curve, application of the nucleation pulse to initiate the plating process dramatically improves the consistency and repeatability of plating potential measurement data, as shown in FIGS. 6A (no nucleation pulse) and 6B (employing a nucleation pulse). Referring to FIG. 6A, the group of curves labeled "basis solution" depict the plating potential of the base metal plate bath, with no additives. The curve labeled "sample" shows the response of the base metal plate bath with the sample of suppressor to be measured added therein. The remaining curbs, collectively labeled "standard additions" depict the responses for each of several standard additions of suppressor additive added to the base metal plate bath to generate data from which the concentration of suppressor additive in the sample is determined according to the methodology of the present invention.

FIG. 6A depicts the scrambling of data obtained during the standard addition measurements with no nucleation pulse. Reliable extrapolation of sample suppressor additive concentration is difficult due to the wide variation in the response curves.

Figure 6B:
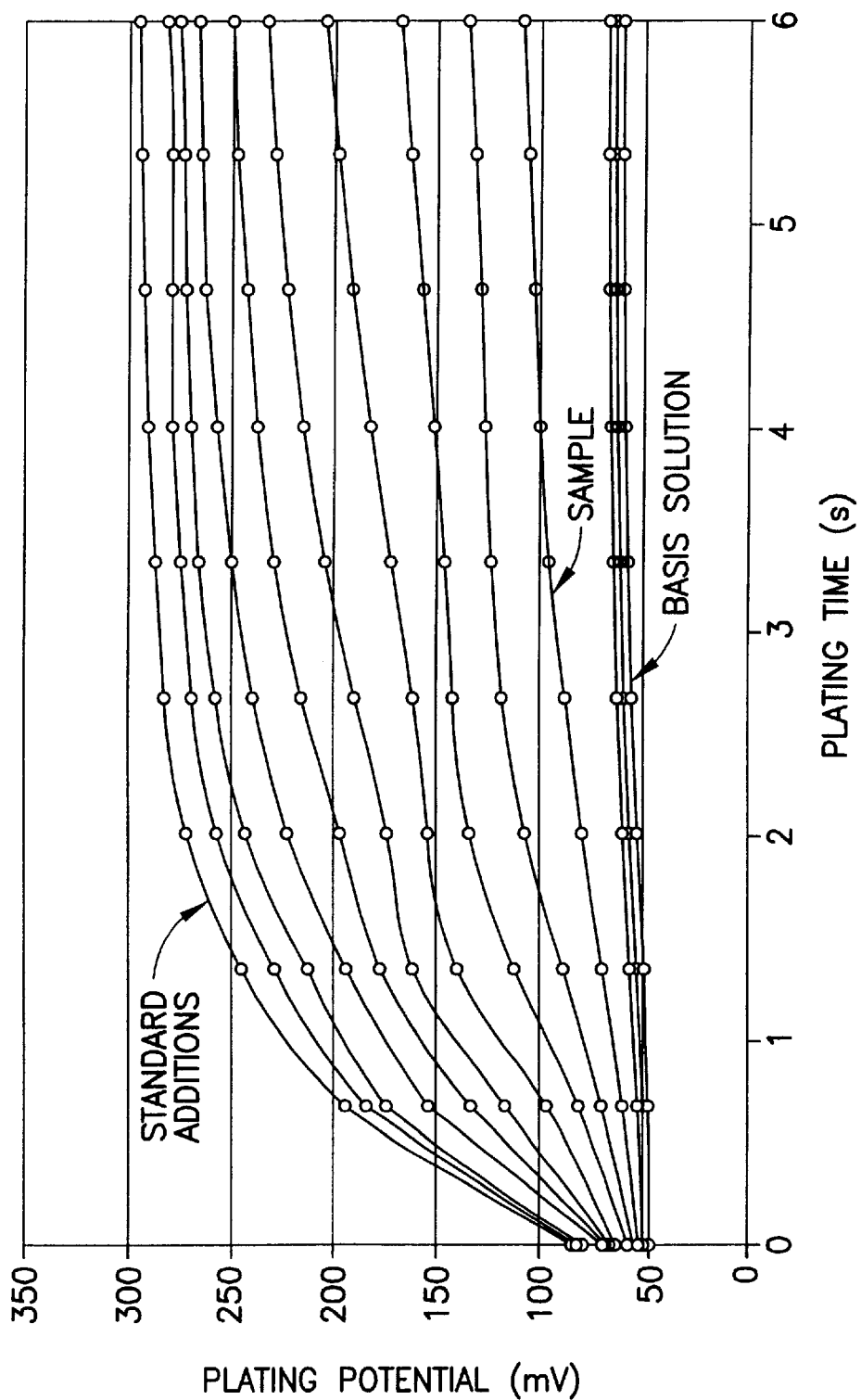
FIG. 6B is a graph depicting the same measurements as FIG. 6A, utilizing the nucleation pulse technique.
Figure 7:
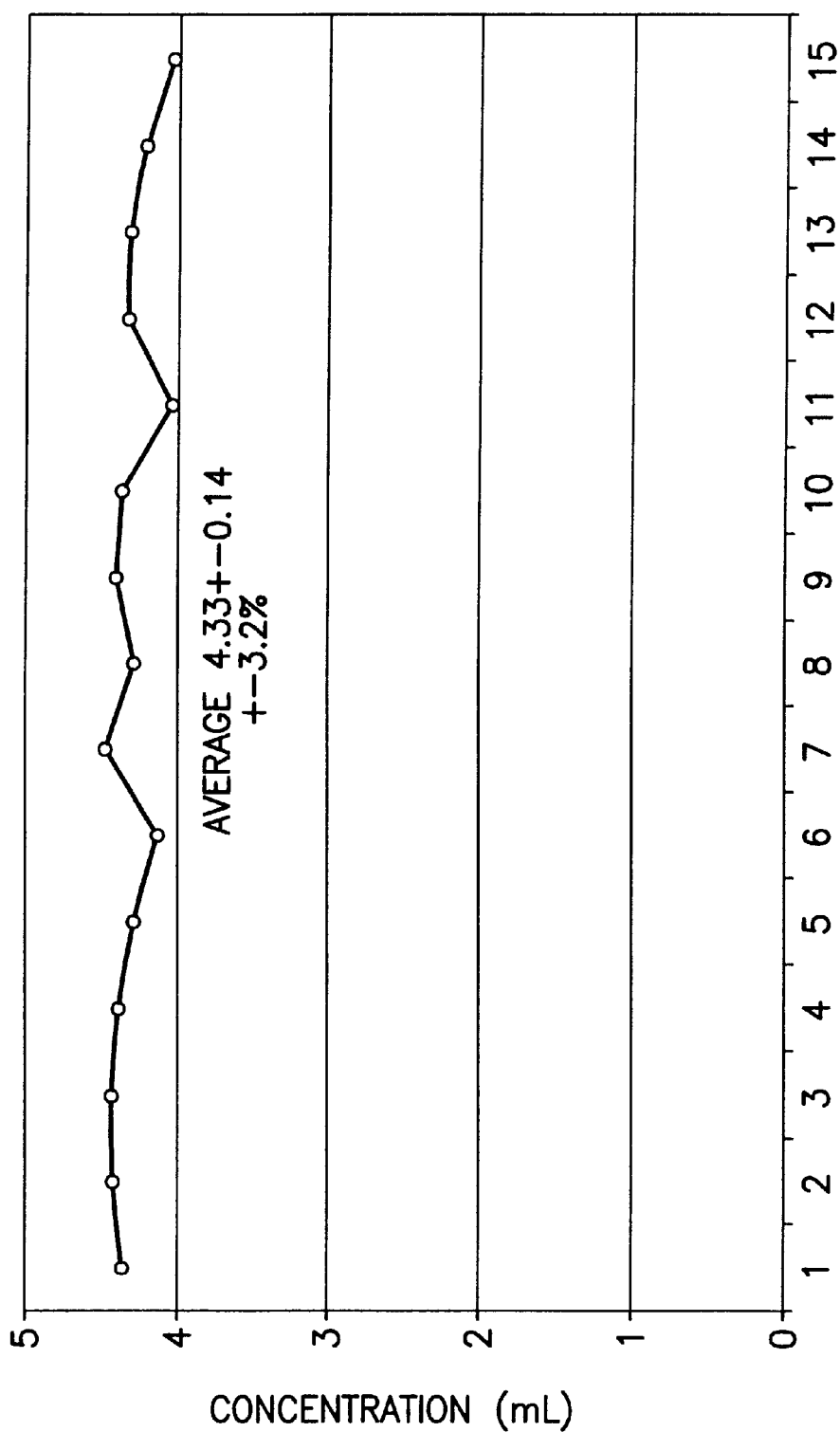
FIG. 7 is a graph depicting the repeatability of measurements taken utilizing the nucleation pulse technique.

FIG. 6B depicts the same set of curves (correspondingly labeled) wherein the plating process was initiated with a nucleation pulse. Utilization of the nucleation pulse obviates the need for suppressor conditioning of the base metal plate bath to avoid nonlinearity of response, as discussed above (hence all of the curves of FIG. 6B originating at or near the same initial plating potential). The orderly separation of the curves and generally "well-behaved" distribution of data points demonstrate the value of the nucleation pulse to the methodology of the present invention. The repeatability of additive concentration measurements performed utilizing the nucleation pulse is demonstrated by reference to FIG. 7, depicting the analysis results for a nominal 5 mL/L suppressor additive solution, wherein an average concentration of 4.33 mL/L was measured, with a variation of only 3.2%.

With increased linearity of the additive response curve in the low concentration region achieved by employing the two-phase metal plating process, the concentration of the organic additive in the sample metal plating solution can also be determined more accurately by interpolative PCGA method rather than by extrapolation. This is easily achieved by first preparing calibration solutions containing the additive in various concentrations from below what will be expected in the sample solution to above such expected sample concentration, then doing all the measurements of the calibration solutions to following the background measurement of the basis solution to build up a calibration curve characteristic of the particular additive, and finally measuring a fresh sample or diluted sample and interpolating the concentration of additive in such sample solution from the already plotted calibration curve. For this technique to be accurate it is particularly necessary to ensure that the background and calibration measurements are done in a matrix that closely matches the sample solution in all components (or PCGA characteristics), except the additive whose concentration is to be determined.

In one embodiment of the present invention, the concentrations of both accelerator and suppressor organic additives in copper-metal semiconductor plating electrolyte baths are determined in a single extrapolative PCGA analysis, as follows (wherein each step calling for a plating/measuring cycle including an initial nucleation pulse is actually performed multiple times (e.g., four times) and the results averaged, to eliminate random errors):

1) Perform a plating/measuring cycle including an initial nucleation pulse in a base copper plating electrolyte solution ("basis solution") which contains all of the components of the plating solution to be measured (the "sample"), with the exception of accelerator and suppressor organic additives. This is the background measurement for the suppressor additive concentration determination. Optionally and ideally the background measurement is made in the presence of a known volume addition of the additive (suppressor) whereby this measurement and all following decisive potentials measured are in a linear section of the response curve.

2) Add a small amount of sample (preferably less than 1 ml and greater than 0.01 ml and most preferably about 0.1 ml) to a known fixed volume (the "standard volume" which is less than 100 ml and preferably 10 ml) of basis solution, and perform a plating/measuring cycle including an initial nucleation pulse in the mixed solution.

3) Add a first standard addition of suppressor additive to a standard volume of fresh basis solution, and perform a plating/measuring cycle including an initial nucleation pulse in the mixed solution.

4) Repeat step 3 using at least a second standard addition of suppressor additive, and optionally a third, fourth, etc., standard addition.

5) Add an excess of suppressor additive to a standard volume of fresh basis solution, and perform a plating/measuring cycle including an initial nucleation pulse in the mixed solution. This is the background measurement for the accelerator additive concentration determination.

6) Add a larger amount of sample to a standard volume of basis solution containing the excess of suppressor additive as in step 5. A greater amount of sample is required than was required for step 2, because of the generally lower sensitivity of the plating process to the accelerator additive than the suppressor additive. Perform a plating/measuring cycle including an initial nucleation pulse in the mixed solution.

The volumes of additives that must be employed are dependent on the concentrations set by the bath manufacturer and must therefore be adjusted accordingly, as may be performed without undue experimentation by those of ordinary skill in the art.

7) Add a first standard addition of accelerator additive to a standard volume of basis solution containing the excess of suppressor additive as in step 5, and perform a plating/measuring cycle including an initial nucleation pulse in the mixed solution.

8) Repeat step 7 using at least a second standard addition of accelerator additive and optionally a third, fourth, etc., standard addition.

9) Analyze the measured data for the suppressor and accelerator additives separately, according to the methodology described hereinabove, to extrapolatively determine the suppressor and accelerator additive concentrations in the sample.

Figure 8:
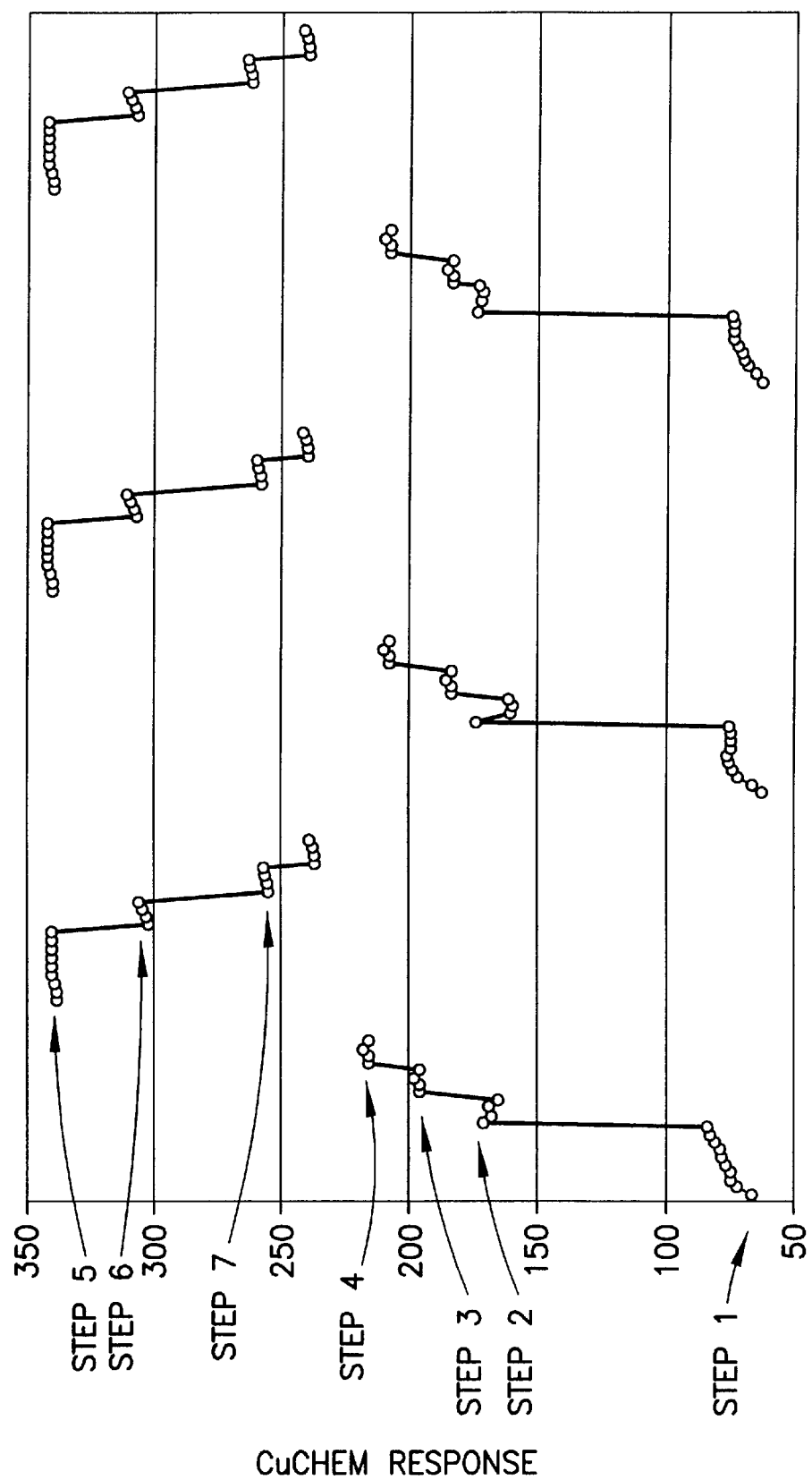
FIG. 8 is a graph depicting a suppressor/accelerator concentration determination according to one embodiment of the present invention.

The graph of FIG. 8 is representative of the data obtained from a suppressor/accelerator concentration determination according to this process, wherein the data are labeled to correspond to the above-described steps.

In a further embodiment of the present invention, the concentrations of accelerator and suppressor additives in the copper-metal plating solution can be determined with improved accuracy in an interpolative PCGA analysis, comprising the steps of:

1) perform a plating/measuring cycle including an initial nucleation pulse in the basis solution, optionally the basis solution is conditioned by a known volume addition of suppressor so that this measurement and all following decisive potentials measured are in a linear section of the response curve. This is the background measurement for the suppressor additive concentration determination;

2) Add a first standard addition of suppressor additive to a standard volume (which is less than 100 ml and preferably 10 ml) of basis solution, and perform a plating/measuring cycle including an initial nucleation pulse in the mixed solution;

3) Repeat step 2 using at least a second standard addition of suppressor additive, and optionally a third, fourth, etc., standard addition;

4) Add a small amount of sample (preferably less than 1 ml and greater than 0.01 ml and most preferably about 0.1 ml) to a standard volume of fresh basis solution, and perform a plating/measuring cycle including an initial nucleation pulse in the mixed solution;

5) Add an excess of suppressor additive to a standard volume of fresh basis solution, and perform a plating/measuring cycle including an initial nucleation pulse in the mixed solution. This is the background measurement for the accelerator additive concentration determination.

6) Add a first standard addition of accelerator additive to a standard volume of basis solution containing the excess of suppressor additive as in step 5, and perform a plating/measuring cycle including an initial nucleation pulse in the mixed solution;

7) Repeat step 6 using at least a second standard addition of accelerator additive and optionally a third, fourth, etc., standard addition;

8) Add a larger amount of sample to a standard volume of basis solution containing the excess of suppressor additive as in step 5. A greater amount of sample is required than was required for step 4 as well. Perform a plating/measuring cycle including an initial nucleation pulse in the mixed solution.

9) Analyze the measured data for the suppressor and accelerator additives separately, and interpolate the sample concentrations of suppressor and accelerator from the measured data using the above introduced interpolation method.

The invention will be further understood and illustrated by the following non-limiting examples.

EXAMPLE 1

In addition to the measuring vessel described above, the analyzer consists of 4 digital burettes that are filled with the following solutions

| Burette 1 | the sample itself collected from an overflow sample capture vessel |
|---|---|
| Burette 2 | diluted (25 x) accelerator additive |
| Burette 3 | diluted (25 x) suppressor |
| Burette 4 | the base solution composed of |
| | 70 g/l cupric sulfate pentahydrate |
| | 180 g/l 95–97% sulfuric acid |
| | 60 ppm chloride as hydrochloric acid |

The analyzer was programmed to perform the following sequence. The overall operation given in terms of the actual command code used on the analyzer was as follows:

| 1  | 2   | 3    | 4    | 5   | 6   | 7   | 8  | 9   | 10  | 11  |
|----|-----|------|------|-----|-----|-----|----|-----|-----|-----|
| C3 | S20 | C3   | FIL  | Bsp | INs | SUP | C3 | Bac | INa | ACC |
| 0.1| 0.1 | 0.04 | 4 10.0 |   | 0.4 | 3   | 2.0|     | 6.0 | 2   |

This sequence of commands has the following significance:
1 C3 a pre-analysis step to prime the dispensing tip of burette 3 by dispensing 0.1 ml
2 S20 a sampling operation in which burette 1 is filled with fresh sample and the dispensing tube (using flow segregation) with 1 ml of a 20×diluted sample
3 C3 the background level for the suppressor determination is raised by adding 0.04 ml of diluted suppressor from burette 3
4 FIL the measurement vessel is filled with 10 ml of the basis solution from burette 4
5 Bsp the background measurement for the suppressor is carried out. This command performs the clean, equilibrate, plate and strip operations
6 INs 0.4 ml of diluted sample is added
7 SUP the suppressor measurement is carried out using the standard addition procedure and repeated clean, equilibrate, plate and strip operations. Burette 3 is used for the standard additions of diluted suppressor
8 C3 an excess of suppressor (2 ml) is added to prepare for the accelerator determination
9 Bac the background measurement for the accelerator is carried out. This command performs the clean, equilibrate, plate and strip operations
10 INa 6.0 ml of the sample is added—the remaining diluted sample is injected first followed by the pure sample. The injection volume is automatically corrected (increased) by the appropriate amount to account for the part injection of diluted sample.
11 ACC the accelerator is measured with standard addition procedure and repeated clean, equilibrate, plate and strip operations. Burette 2 is used for the standard additions of diluted accelerator.

The clean, equilibrate, plate, strip cycle used for the suppressor background measurement (Bsp) the accelerator background measurement (Bac) and the suppressor and accelerator measurements themselves (SUP), (ACC) is as follows:

| | |
|---|---|
| Clean | the test electrode is polarized anodically with a current of 2 mA for 10 seconds |
| Equilibrate | the test electrode is left to equilibrate at zero current for 20 seconds |
| Plate | the test electrode is polarized cathodically at 1 mA for 10 seconds |
| Strip | (optional) the test electrode is polarized anodically with a current of 1 mA for 1 second |

Figure 9:
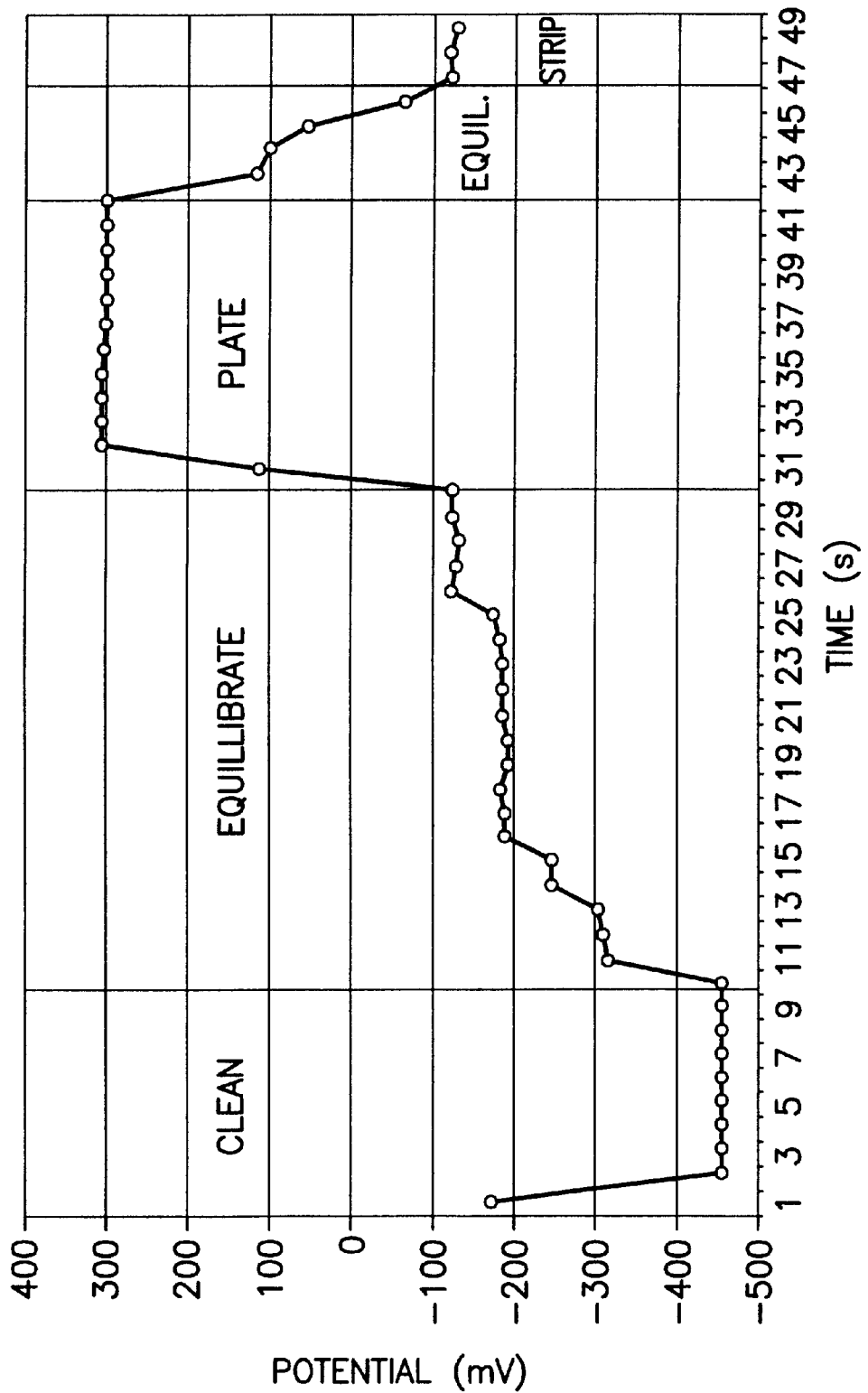
FIG. 9 shows the response curve during the clean, equilibrate, plate and strip cycles according to one embodiment of the present invention.
Figure 10:
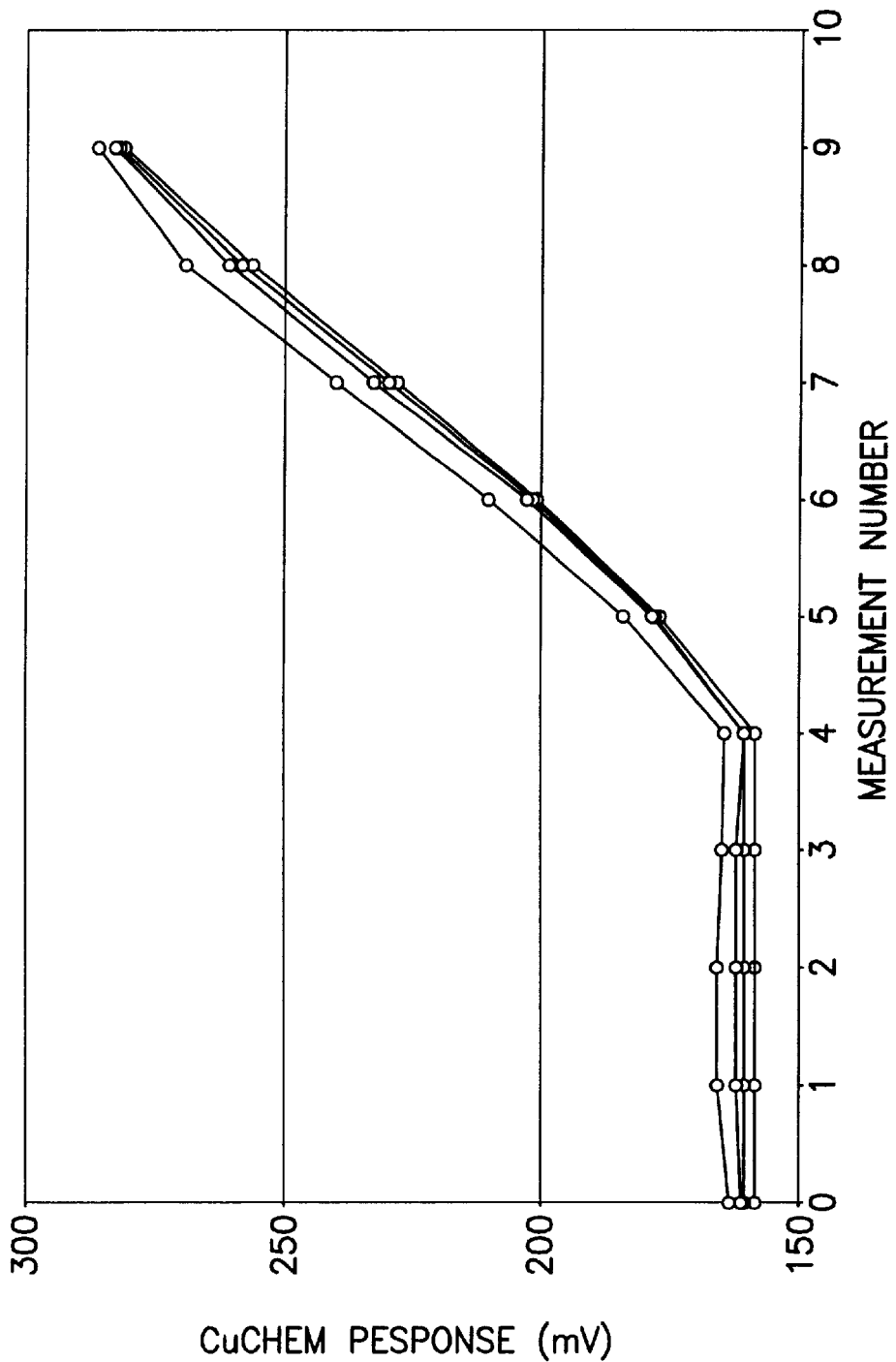
FIG. 10 shows the response for the suppressor additive measurement according to one embodiment of the present invention.
Figure 11:
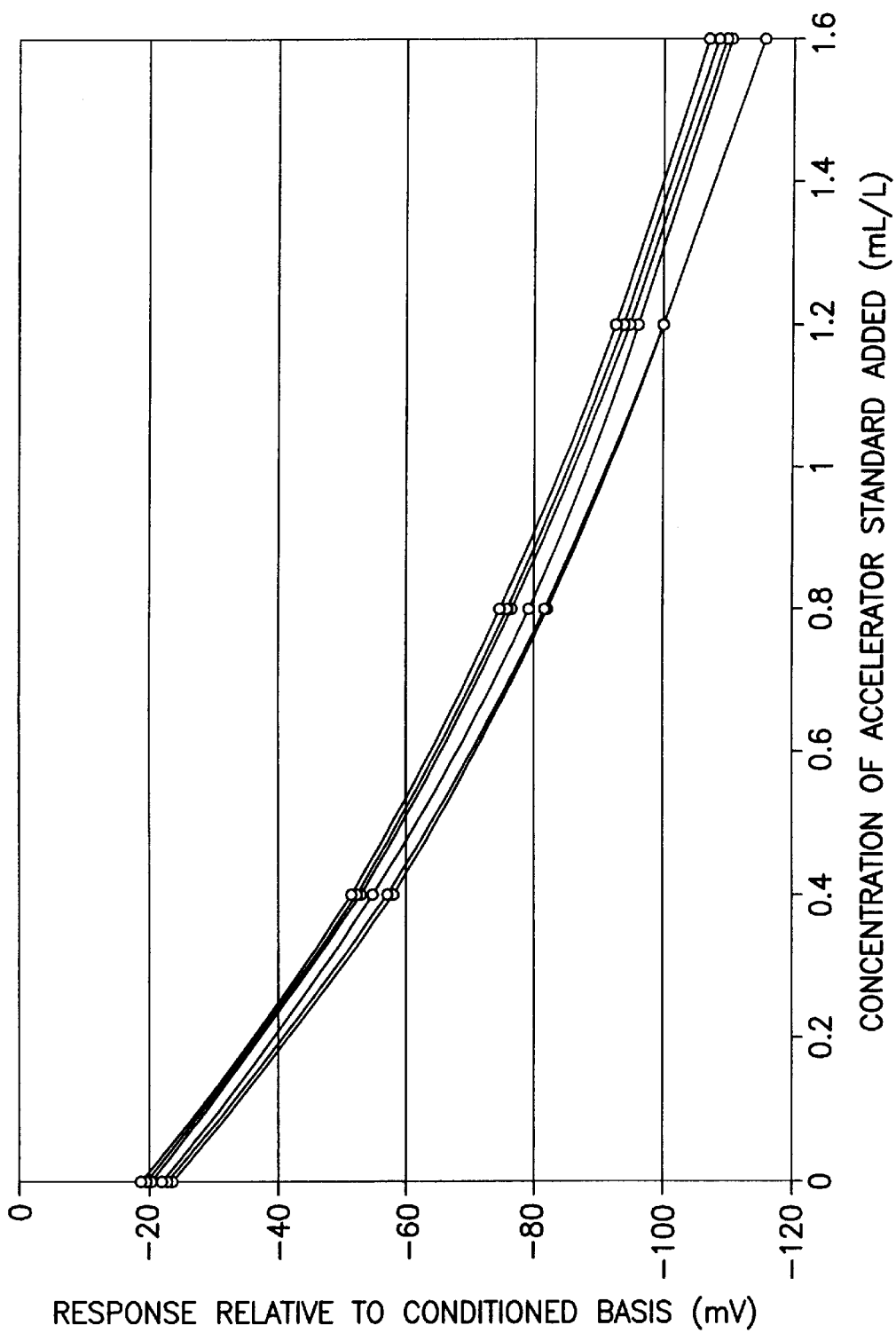
FIG. 11 shows the response for the accelerator additive measurement according to one embodiment of the present invention.

FIG. 9 shows the response curve during the clean, equilibrate, plate and strip cycles. The potential is measured at the reference electrode with the test electrode grounded.
FIG. 10 shows the response for the suppressor additive measurement.
FIG. 11 shows the response to the accelerator additive measurement.
Typically the results obtained from these measurements were:
Suppressor 26.4 ml/l
Accelerator 1.05 ml/l

EXAMPLE 2

For measuring a sample solution containing 25 ml/L suppressor additive and 1.0 ml/L accelerator additive, the analyzer used consists of 4 digital burettes that are filled with the following solutions:
Burette 1: diluted (100×) sample solution
Burette 2: accelerator standard additive
Burette 3: suppressor standard additive
Burette 4: the basis solution composed of
70 g/L copper sulfate
180 g/L sulfuric acid
60 ppm chloride
The analyzer has been programmed to perform the following sequences:

| 1  | 2    | 3  | 4   | 5   | 6   | 7  | 8   | 9   | 10  | 11 |
|----|------|----|-----|-----|-----|----|-----|-----|-----|----|
| M1 | FIL  | C3 | Bsp | Ins | SUP | C3 | Bac | Ina | ACC | M1 |
|    | 4 10.0 |  | 0.1 | 3   | 5.00 |   |     | 5.00 | 2   |    |

The clean, equilibrate, plate, strip cycle and the nucleation pulse used for all the measurements are established as follows:

|             | CLEAN | EQUIL. | PLATE  | STRIP  | PULSE              |
|-------------|-------|--------|--------|--------|--------------------|
| Accelerator | 0 sec | 20 sec | 18 sec | 10 sec | 7 ticks (140 msec) |
| Suppressor  | 0 sec | 20 sec | 6 sec  | 10 sec | 7 ticks (140 msec) |

|                        | Accelerator | Suppressor |
|------------------------|-------------|------------|
| Standard Additions:    | 3           | 4          |
| Standard Concentration:| 10          | 25         |
| Step:                  | 0.5         | 0.1        |
| Equilibrium Cycles:    | 1           | 5          |
| Averaging:             | last 2      | last 1     |
| Back Cycles:           | 5           | 5          |
| Polynomial Order:      | 2           | 2          |

Figure 12:
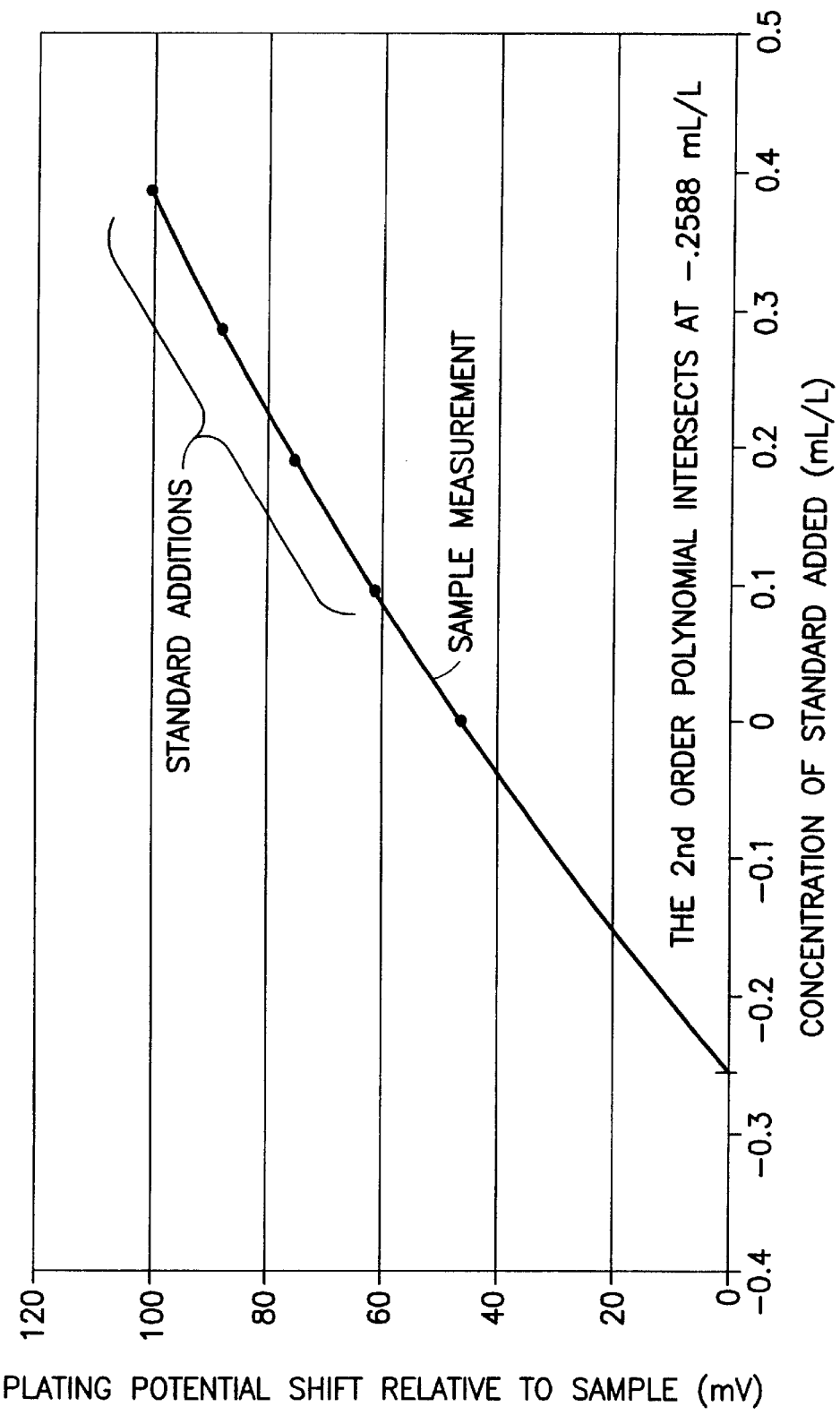
FIG. 12 is a graph depicting an extrapolative suppressor concentration determination using pulse nucleation technique during the plating process.

The current density of the pulse to initiate nucleation is set at. 400 mA/cm$^2$. The rotating disc electrode is set at the speed of 1250 rpm.
The commands of the analysis has the following significance:
1 M1 The measurement chamber is emptied
2 FIL The measurement chamber is filled with 10.0 ml of the basis solution from burette 4
3 C3 A small amount of suppressor additive is added to condition the basis solution
4 Bsp A PCGA cycle is performed to obtain the background measurement for suppressor concentration determination
5 INs 0.1 ml of diluted sample is added to the measurement chamber. A PCGA measurement is carried out on the sample
6 SUP The suppressor measurement is carried out using the standard addition procedure and repeated clean, equilibrate, plate, and strip operations. Burette 3 is used for the standard additions of suppressor additive
7 C3 An excess of suppressor (5 ml) is added to the basis solution to prepare for the accelerator determination
8 Bac A PCGA cycle is performed to obtain the background measurement for accelerator concentration determination 9 INa 5 ml of diluted sample is added to the measurement chamber. A PCGA measurement is carried on the sample 10 ACC The accelerator measurement is carried out using the standard addition procedure and repeated clean, equilibrate, plate, and strip operations. Burette 2 is used for the standard additions of accelerator additive 11 M1 The following commands serve to flush out the cell and remove traces of the organic additives in preparation for the next analysis FIG. 12 shows that the concentration of suppressor additive obtained by extrapolation of a second order polynomial is 0.2588 ml/L in the measuring vessel for a 100 times dilution of the sample, which means 25.88 ml/L in the sample solution. Using the same technique, the accelerator additive concentration is determined to be 1.05 ml/L (not shown).

EXAMPLE 3

In this example, interpolative PCGA determination of concentrations of suppressor and accelerator additives in sample solution has been carried out for measuring a sample solution containing both suppressor additive and accelerator additive. In programming for different concentrations, the total volume of the mixed solution to be measured is constantly fixed at approximately 10 ml, and only the sample size added is changed. For example, if 3 ml of sample solution shall be added, 7 ml of basis solution will be added to fill up the measurement chamber to come up with 10 ml of mixed solution in total. Notice that the mixing of sample solution with basis solution actually dilutes the sample solution, and the concentration of additives measured by interpolation is therefore the diluted concentration. The real concentration of additives in the sample solution can be easily calculated therefrom.

The analyzer used in this example also consists of 4 digital burettes that are filled with the following solutions:

| | |
|---|---|
| Burette 1: | sample solution |
| Burette 2: | accelerator standard addition |
| Burette 3: | suppressor standard addition |
| Burette 4: | the basis solution composed of |
| | 70 g/L copper sulfate |
| | 180 g/L sulfuric acid |
| | 60 ppm chloride |

The analyzer has been programmed to perform the following sequences:

| FIL | Bsp | Csp | M1 | FIL | INs | M1 | FIL | Bac | Cac | M1 | FIL | INa | M1 |
|---|---|---|---|---|---|---|---|---|---|---|---|---|---|
| 4 | 3 | 4 | | 0.25 | 3 | | | 2 | 3 | | 3.0 | | |
| 10.0 | | 10.0 | | | 10.0 | | | | 7.0 | | | | |

The clean, equilibrate, plate, strip cycle and the nucleation pulse used for all the measurements are established as follows:

| | CLEAN | EQUIL. | PLATE | STRIP | PULSE |
|---|---|---|---|---|---|
| Accelerator | 0 sec | 20 sec | 18 sec | 15 sec | 5 ticks (100 msec) |
| Suppressor | 0 sec | 20 sec | 5 sec | 10 sec | 5 ticks (100 msec) |

| | Accelerator | Suppressor |
|---|---|---|
| Standard Additions: | 5 | 5 |
| Standard Concentration: | 10 | 25 |
| Step: | 0.1 | 0.15 |
| Equilibrium Cycles: | 1 | 1 |
| Averaging: | last 1 | last 1 |
| Back Cycles: | 1 | 1 |
| Polynomial Order: | 2 | 2 |

The current density of the pulse to initiate nucleation is set at 400 mA/cm$^2$. The rotating disc electrode is set at the speed of 1250 rpm.

The commands of the analysis has the following significance:

1 FIL The measurement chamber is filled with 10 ml of the basis solution from burette 4

2 Bsp A PCGA cycle is performed to obtain the background measurement for suppressor additive concentration determination 3 Csp A multiple PCGA cycles are performed using standard additions of suppressor from burette 3 to build up the calibration curve of suppressor additive and fit a calibration polynomial to the data 4 M1 The measurement chamber is emptied 5 FIL 10 ml of basis solution from burette 4 is refilled to the measurement chamber.

6 INs 0.25 ml sample solution is introduced into the measurement chamber from a burette or alternatively from a sampling valve. Notice that the sample solution becomes diluted by approximately 40 times hereby. A PCGA measurement is carried out on the mixed solution containing sample and the basis solution, and its concentration of suppressor can be determined by interpolation of the already plotted calibration curve of suppressor additive. Such interpolated concentration times 40 will result in the real concentration of suppressor additive in the sample solution. (Note that the interpolative technique integrates the actual PCGA measurement within this sample inject command in contrast to examples 1 and 2.)

7 M1 The measurement chamber is emptied.

8 FIL The measurement chamber is filled with 10 ml of standard addition of suppressor from burette 3, which will be used as the basis solution containing excess of suppressor for the accelerator concentration determination and to ensure that the suppressor standards in the background measurement and in the sample measurement are approximately the same.

9 Bac A PCGA is performed to obtain background measurement data for accelerator additive concentration determination.

10 Cac Multiple PCGA cycles are performed upon standard additions of accelerator additive from burette 2 to build up the calibration curve characteristic of accelerator additive and to fit a calibration polynomial to the data 11 M1 The measurement chamber is emptied.

12 FIL The measuring chamber is refilled with 7 ml of the suppressor standard addition from burette 3

13 INa 3 ml of sample solution is added to the measurement chamber. Notice that the sample solution becomes diluted by approximately 3.3 times hereby. A PCGA measurement is carried out on the mixed solution containing sample and the basis solution with excess of suppressor, and its concentration of accelerator additive can be determined by interpolation of the already plotted calibration curve of accelerator additive. Such interpolated concentration times 3.3 will result in the real concentration of accelerator additive in the undiluted sample solution. (Note that the interpolative technique integrates the actual PCGA measurement within this sample inject command in contrast to examples 1 and 2.)

14 M1 This command serve to flush out the cell and remove traces of the organic additives in preparation for the next analysis.

Figure 13A:
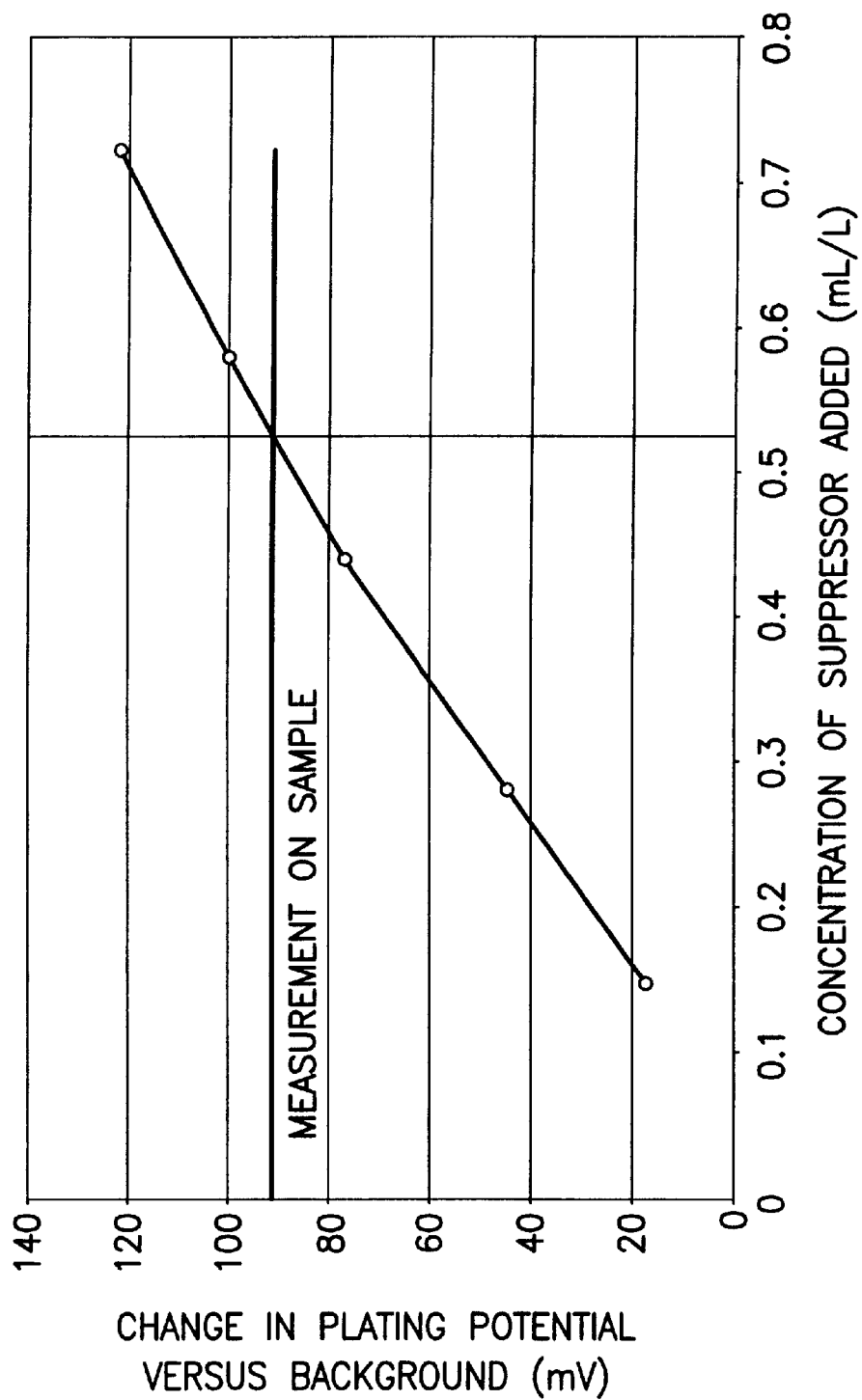
FIG. 13A is a graph depicting an interpolative suppressor concentration determination using pulse nucleation technique during the plating process.

FIG. 13A shows that the interpolated concentration of suppressor additive in the mixed solution is approximately 5.5 ml/L, which indicates that the concentration of suppressor in the undiluted sample solution will be approximately 22 ml/L (=5.5 ml/L×40).

Figure 13B:
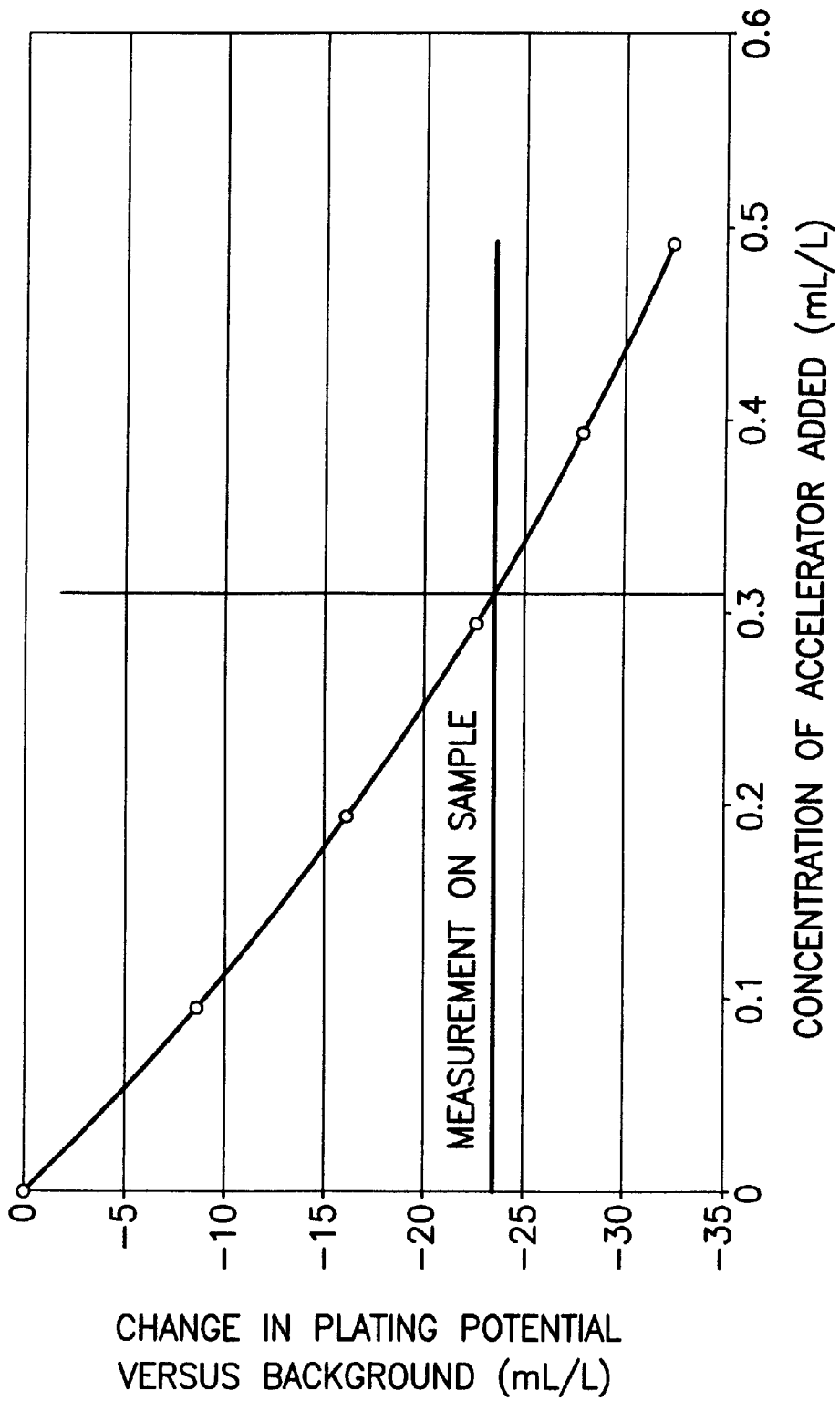
FIG. 13B is a graph depicting an interpolative accelerator concentration determination using pulse nucleation technique during the plating process.

FIG. 13B shows that the interpolated concentration of accelerator additive in the mixed solution is approximately 0.31 ml/L, which indicates that the concentration of accelerator in the undiluted sample solution will be approximately 1.032 ml/L (=0.31 ml/L×3.3).

The following chart shows experimental results obtained from a series of study and analysis employing pulse nucleation technique, interpolation PCGA method, and the above-specified apparatus and procedure. Such analysis was operated 24 hours a day over one week operation:

| Acc. (ml/L) | Supp. (ml/L) | INa (ml) | INs (ml) | Measured Acc. (ml/L) | Measured Supp. (ml/L) |
|---|---|---|---|---|---|
| 1 | 12.5 | 3.00 | 0.50 | 1.090 ± 0.026 (2.4%) | 12.15 ± 0.25 (2.0%) |
| 1 | 25 | 3.00 | 0.25 | 1.011 ± 0.023 (2.3%) | 25.98 ± 0.61 (2.4%) |
| 1 | 37.5 | 3.00 | 0.15 | 1.096 ± 0.021 (1.9%) | 37.79 ± 1.07 (2.8%) |
| 3 | 25 | 1.00 | 0.25 | 3.06 ± 0.060 (2.0%) | 26.75 ± 0.75 (2.8%) |
| 5 | 12.5 | 0.60 | 0.50 | 5.69 ± 0.10 (1.7%) | 12.32 ± 0.30 (2.4%) |
| 5 | 37.5 | 0.60 | 0.15 | 5.39 ± 0.10 (1.9%) | 41.41 ± 1.62 (3.9%) |

The above-disclosed measurement data prove significant improvements made by present invention over the prior art.

Although the invention has been variously disclosed herein with reference to illustrative embodiments and features, it will be appreciated that the embodiments and features described hereinabove are not intended to limit the invention, and that other variations, modifications and other embodiments will suggest themselves to those of ordinary skill in the art. The invention therefore is to be broadly construed, consistent with the claims hereafter set forth.

What is claimed is:

1. An apparatus for determining the concentration of additives in a metal plating bath, comprising:

a reference electrode, housed in an electrically isolated reference chamber and immersed in a base metal plating solution;

a test electrode having a plating surface upon which metal is depositable by electroplating, disposed in a measurement chamber containing an electroplating current source electrode, wherein metal plating solutions containing known and unknown concentrations of additives are introduced to, and intermixed with, the base metal plating solution to form a mixed metal plating solution;

a capillary tube joining the reference chamber and the measurement chamber in unidirectional fluid flow relationship, having a reference chamber end disposed in the reference chamber and a measurement chamber end disposed in the measurement chamber, whereby base metal plating solution is transferred to the measurement chamber from the reference chamber, and wherein the measurement chamber end of the capillary tube is disposed in close spatial relationship to the plating surface of the test electrode;

selectively controllable electroplate driving electronics electrically and operatively coupled between the test electrode and the electroplating current source electrode, for selectively effectuating deposition of metals onto the test electrode from the mixed metal plating solution in the measurement chamber, wherein said electroplate driving electronics have two selectable modes, the first mode for providing an initial high plating current density for a short duration, and the second mode for providing subsequent constant or known current density for a duration sufficient to measure electrical potential; and electrical potential measuring circuitry electrically and operatively coupled between the test electrode and the reference electrode, whereby electrical potential between the test electrode and the reference electrode is measured and recorded.

2. The metal plating bath analysis apparatus of claim 1, wherein the test electrode is selected from the group consisting of rotating disc electrodes and ultra-micro electrodes.

3. The metal plating bath analysis apparatus of claim 1, wherein the test electrode is operatively coupled to a hydrodynamic actuator such that a reproducible flow of mixed metal plating solution in the measurement chamber is directed against an operative surface of said test electrode.

4. The metal plating bath analysis apparatus of claim 3, wherein the hydrodynamic actuator is selected from the group consisting of ultrasonic vibrators, mechanical vibrators, propellers, pressure differential fluid pumps, static mixers, gas spargers, magnetic stirrers, fluid ejectors, and fluid eductors.

5. The metal plating bath analysis apparatus of claim 1, wherein the test electrode is deposed within the measuring chamber at an acute angle between 3 and 45 degrees from vertical.

6. The metal plating bath analysis apparatus of claim 1, wherein the test electrode comprises a material selected from the group consisting of noble metals and glassy carbon.

7. The metal plating bath analysis apparatus of claim 6, wherein the noble metals comprise metals selected from the group consisting of platinum and gold.

8. The metal plating bath analysis apparatus of claim 1, wherein the first mode of the electroplate driving electronics provides an initial high current density in the range from 10 mA/cm$^2$ to 10 A/cm$^2$.

9. The metal plating bath analysis apparatus of claim 1, wherein the first mode of the electroplate driving electronics provides an initial high current density about 400mA/cm$^2$.

10. The metal plating bath analysis apparatus of claim 1, wherein the first mode of the electroplate driving electronics provides an initial high current density for a duration in the range from 1 msec to 1000 msec.

11. The metal plating bath analysis apparatus of claim 1, wherein the first mode of the electroplate driving electronics provides an initial high current density for a duration in the range from 40 msec to 200 msec.

12. A method of measuring a characteristic decisive potential of a mixed metal plating solution by performing a plating/measuring cycle, comprising:

provRead an apparatus as in claim 1;

cleaning the test electrode and measuring chamber;

flowing a first known volume of base metal plating solution which contains all components of the mixed metal plating solution to be measured except a component of interest from the reference chamber through the capillary tube into the measurement chamber;

optionally adding to the measurement chamber a second known volume of metal plating solution containing a predetermined or unknown concentration of the component of interest and mixing the solutions;

allowing the test electrode to come to an equilibrium state in the mixed metal plating solution, such that no electric current flows to or from the test electrode;

depositing metal onto the test electrode from the mixed metal plating solution in the measurement chamber by a two-phase electroplating process, comprising an initial first phase in which electroplating occurs at a high plating current density for a first duration, and a subsequent second phase in which electroplating occurs at a constant or known current density for a second duration;

measuring and recording the decisive electrical potential between the reference electrode and the test electrode at a selected time after initiation of the second phase of the plating step, whereby sufficient stability has been reached;

stripping the deposited metal from the test electrode.

13. The plating/measurement cycle method of claim 12, wherein the cleaning step comprises a step selected from the group consisting of acid bath exposure, water flush, forced fluid purge, and combinations thereof.

14. The plating/measurement cycle method of claim 12, wherein the current density of the first phase of the electroplating process is in the range from 10 mA/cm$^2$ to 10 A/cm$^2$.

15. The plating/measurement cycle method of claim 12, wherein the current density of the first phase of the electroplating process is about 400 mA/cm$^2$.

16. The plating/measurement cycle method of claim 12, wherein the first duration of the electroplating process is in the range from 1 msec to 1000 msec.

17. The plating/measurement cycle method of claim 12, wherein the first duration of the electroplating process is in the range from 40 msec to 200 msec.

18. The plating/measurement cycle method of claim 12, wherein the stripping step comprises a step selected from the group consisting of chemical stripping, application of reverse bias electroplating current, and combinations thereof.

19. The plating/measuring cycle method of claim 12, further comprising:

measuring and recording an equilibrium electrical potential between the reference electrode and the test electrode following the plating process, with zero current flow in the electroplating circuit; and subtracting the equilibrium potential from the decisive potential to obtain an over-potential.

20. A Pulsed Cyclic Galvanostatic Analysis method for extrapolatively calculating the concentration of a component of interest in a sample of metal plating solution, comprising the steps of:

preparing a basis metal plating solution which contains all components of the sample plating solution to be measured, except the component of interest, or optionally to which has been added a known volume of the component of interest;

preparing a plurality of calibration solutions, each of which contains the component of interest in a unique, known concentration in excess of that which would be expected in the sample solution;

performing a plating/measuring cycle including an initial nucleation pulse in the basis solution, and measuring the decisive potential characteristic of the basis solution;

adding a measured amount of the sample solution to a known volume of the basis solution, performing a plating/measuring cycle including an initial nucleation pulse in the mixed solution, and measuring the decisive potential characteristic of the mixed solution;

adding a measured amount of the first calibration solution to the same volume of fresh basis solution, performing a plating/measuring cycle including an initial nucleation pulse in the mixed solution, and measuring the decisive potential of the mixed solution;

repeating the above step for each calibration solution, measuring the decisive potential of each; and plotting the reciprocals of the decisive potentials measured on a reciprocal concentration scale, and performing a linear extrapolation back to the basis measurement to obtain the negative reciprocal of the sample concentration of the component of interest; or as an alternative, fitting a polynomial to the decisive potentials for the component of interest as a function of the volumes of the calibration solutions added, and extrapolating the polynomial back to zero decisive potential to obtain the negative sample concentration of the component of interest.

21. The Pulsed Cyclic Galvanostatic Analysis method of claim 20, wherein each plating/measuring cycle including an initial nucleation pulse is performed a plurality of times, and the decisive potentials measured during each cycle are averaged.

22. The Pulsed Cyclic Galvanostatic Analysis method of claim 20, wherein the potential measured during each plating/measuring cycle including an initial nucleation pulse is the over-potential, obtained by:

measuring and recording, during each plating/measuring cycle including an initial nucleation pulse, an equilibrium electrical potential between the reference electrode and the test electrode following the plating step, with zero current flow in the electroplating circuit; and subtracting the equilibrium potential from the decisive potential to obtain the over-potential.

23. A Pulsed Cyclic Galvanostatic Analysis method for interpolatively calculating the concentration of a component of interest in a sample of metal plating solution, comprising the steps of:

preparing a basis metal plating solution which contains all components of the sample plating solution to be measured, except the component of interest, or optionally to which has been added a known volume of the component of interest;

preparing a plurality of calibration solutions, each of which contains the component of interest in a unique, known concentration, wherein concentrations of the component of interest in all the calibration solutions sufficiently cover a full range from below to above that which would be expected in the sample solution;

performing a plating/measuring cycle including an initial nucleation pulse in the basis solution, and measuring the decisive potential characteristic of the basis solution;

adding a measured amount of the first calibration solution to a known volume of the basis solution, performing a plating/measuring cycle including an initial nucleation pulse in the mixed solution, and measuring the decisive potential characteristic of the mixed solution;

repeating the above step for each calibration solution, measuring the decisive potential of each;

adding a measured amount of the sample solution to the same volume of fresh basis solution, performing a plating/measuring cyclic including an initial nucleation pulse in the mixed solution, and measuring the decisive potential characteristic of the mixed solution;

plotting the reciprocals of the decisive potentials measured for the calibration solutions on a reciprocal concentration scale to build up a decisive potential curve, and then interpolating the reciprocal of the sample concentration of the component of interest from such plotted decisive potential curve using the decisive potential measured for the sample solution; or as an alternative, fitting a polynomial to the decisive potentials for the component of interest as a function of the volumes of the calibration solutions added, and interpolating the sample concentration of the component of interest from such fitted polynomial using the decisive potential measured for the sample solution.

24. The Pulsed Cyclic Galvanostatic Analysis method of claim 23, wherein each plating/measuring cycle including an initial nucleation pulse is performed a plurality of times, and the decisive potentials measured during each cycle are averaged.

25. The Pulsed Cyclic Galvanostatic Analysis method of claim 23, wherein the potential measured during each plating/measuring cycle including an initial nucleation pulse is the over-potential, obtained by:

measuring and recording, during each plating/measuring cycle including an initial nucleation pulse, an equilibrium electrical potential between the reference electrode and the test electrode following the plating step, with zero current flow in the electroplating circuit; and subtracting the equilibrium potential from the decisive potential to obtain the over-potential.

26. A method of extrapolatively determining concentrations of both an accelerator organic additive and a suppressor organic additive in a sample of copper-metal semiconductor plating electrolyte solution, comprising the steps of:

(a) preparing a basis copper plating electrolyte solution containing all of the components of the sample copper plating electrolyte solution to be measured, except the accelerator and suppressor additives, or optionally conditioning such basis solution with a known and small volume of the suppressor additive;

(b) preparing plurality of standard additions containing either suppressor additive or accelerator additive, each of which containing suppressor or accelerator in a unique, known concentration in excess of that which would be expected in the sample copper plating solution;

(c) performing a plating/measuring cycle including an initial nucleation pulse in the basis copper plating solutin to obtain a characteristic decisive potential, which is the background measurement for the suppressor additive concentration determination;

(d) adding a measured amount of the sample copper plating solution to a known and fixed volume of basis solution, and performing a plating/measuring cycle including an initial nucleation pulse in the mixed solution, to obtain a characteristic decisive potential thereof;

(e) adding a first standard addition containing suppressor additive to the same volume of fresh basis solution, and performing a plating/measuring cycle including an initial nucleation pulse in the mixed solution to obtain a characteristic decisive potential thereof;

(f) repeating step (e) for each unique standard addition containing suppressor additive, measuring the characteristic decisive potential of the resulting mixed solution;

(g) adding an excess amount of suppressor additive to the same volume of fresh basis copper plating solution, and performing a plating/measuring cycle including an initial nucleation pulse in the mixed solution, to obtain a characteristic decisive potential, which is the background measurement for the accelerator additive concentration determination;

(h) adding an amount of sample in excess of that utilized in step (d) to the same volume of basis copper plating solution containing the excess amount of suppressor additive, and performing a plating/measuring cycle including an initial nucleation pulse in the mixed solution to obtain a characteristic decisive potential;

(i) adding a first standard addition containing accelerator additive to the same volume of fresh basis copper plating solution containing the excess amount of suppressor additive, and performing a plating/measuring cycle including an initial nucleation pulse in the mixed solution to obtain a characteristic decisive potential;

(j) repeating step (i) for each unique standard addition containing accelerator additive, measuring the characteristic decisive potential of the resulting mixed solution;

(k) separately plotting the reciprocals of the decisive potentials measured for the suppressor additive and for the accelerator additive on reciprocal concentration scales, and performing linear extrapolations back to the background measurements for the suppressor and for the accelerator to obtain the negative reciprocals of the sample concentrations of the suppressor additive and the accelerator additive; or as an alternative, separately fitting polynomials to the decisive potentials for both the suppressor additive and the accelerator additive as function of the volumes of standard additives added, and extrapolating the polynomials back to zero decisive potentials to obtain the negative sample concentrations of suppressor and accelerator.

27. The method of claim 26, wherein each plating/measuring cycle including an initial nucleation pulse is performed a plurality of times, and the decisive potentials measured during each cycle are averaged.

28. The method of claim 26, wherein the potential measured during each plating/measuring cycle including an initial nucleation pulse is the over-potential, obtained by:

measuring and recording, during each plating/measuring cycle including an initial nucleation pulse, an equilibrium electrical potential between the reference electrode and the test electrode following the plating process, with zero current flow in the electroplating circuit; and subtracting the equilibrium potential from the decisive potential to obtain the over-potential.

29. The method of claim 26, wherein the known fixed volume of basis copper plating solution is less than 100 milliliters and the amount of sample copper plating solution added is less than 1 milliliter.

30. The method of claim 26, wherein the known fixed volume of base copper plating solution is about 10 milliliters and the amount of sample copper plating solution added is about 0.1 milliliter.

31. The method of claim 26, wherein the polynomials are quadratic.

32. A method of interpolatively determining concentrations of both an accelerator organic additive and a suppressor organic additive in a sample of copper-metal semiconductor plating electrolyte solution, comprising the steps of:

(a) preparing a basis copper plating electrolyte solution containing all of the components of the sample copper plating electrolyte solution to be measured, except the accelerator and suppressor additives, or optionally conditioning such basis solution with a known and small volume of the suppressor additive;

(b) preparing plurality of standard additions containing either suppressor additive or accelerator additive, each of which containing suppressor or accelerator in a unique, known concentration, wherein concentrations of suppressor and accelerator additives in all the standard additions sufficiently cover a full range from below to above that which would be expected in the sample plating solution;

(c) performing a plating/measuring cycle including an initial nucleation pulse in the basis copper plating solutin to obtain a characteristic decisive potential, which is the background measurement for the suppressor additive concentration determination;

(d) adding a first standard addition containing suppressor additive to a known and fixed volume of basis solution, and performing a plating/measuring cycle including an initial nucleation pulse in the mixed solution to obtain a characteristic decisive potential thereof;

(e) repeating step (d) for each unique standard addition containing suppressor additive, measuring the characteristic decisive potential of the resulting mixed solution;

(f) adding a measured amount of the sample copper plating solution to the same volume of fresh basis solution, and performing a plating/measuring cycle including an initial nucleation pulse in the mixed solution, to obtain a characteristic decisive potential thereof;

(g) adding an excess amount of suppressor additive to the same volume of fresh basis copper plating solution, and performing a plating/measuring cycle including an initial nucleation pulse in the mixed solution, to obtain a characteristic decisive potential, which is the background measurement for the accelerator additive concentration determination;

(h) adding a first standard addition containing accelerator additive to the same volume of basis copper plating solution containing the excess amount of suppressor additive, and performing a plating/measuring cycle including an initial nucleation pulse in the mixed solution to obtain a characteristic decisive potential;

(i) repeating step (h) for each unique standard addition containing accelerator additive, measuring the characteristic decisive potential of the resulting mixed solution;

(j) adding an amount of sample in excess of that utilized in step (f) to the same volume of fresh basis copper plating solution containing the excess amount of suppressor additive, and performing a plating/measuring cycle including an initial nucleation pulse in the mixed solution to obtain a characteristic decisive potential;

(k) plotting the reciprocals of the decisive potentials measured for the standard additions containing the suppressor additive on a reciprocal concentration scale to build up a decisive potential curve for suppressor additive, and then interpolating the reciprocal of the sample concentration of suppressor from such plotted decisive potential curve using the decisive potential measured for the same solution during the suppressor concentration determination; or as an alternative, separately fitting a polynomial to the decisive potentials for the suppressor additive as function of the volumes of standard additions of suppressor additive added, and interpolating the sample concentration of the suppressor from such fitted polynomial using the decisive potential measured for the sample solution during the suppressor concentration determination;

(l) repeating step (k) to interpolatively determine the sample concentration of accelerator using decisive potentials measured during the accelerator concentration determination.

33. The method of claim 32, wherein each plating/measuring cycle including an initial nucleation pulse is performed a plurality of times, and the decisive potentials measured during each cycle are averaged.

34. The method of claim 32, wherein the potential measured during each plating/measuring cycle including an initial nucleation pulse is the over-potential, obtained by:

measuring and recording, during each plating/measuring cycle including an initial nucleation pulse, an equilibrium electrical potential between the reference electrode and the test electrode following the plating process, with zero current flow in the electroplating circuit; and subtracting the equilibrium potential from the decisive potential to obtain the over-potential.

35. The method of claim 32, wherein the known fixed volume of basis copper plating solution is less than 100 milliliters and the amount of sample copper plating solution added is less than 1 milliliter.

36. The method of claim 32, wherein the known fixed volume of base copper plating solution is about 10 milliliters and the amount of sample copper plating solution added is about 0.1 milliliter.

37. The method of claim 32, wherein the polynomials are quadratic.

* * * * *